(12) United States Patent
Yabusaki et al.

(10) Patent No.: US 8,507,282 B2
(45) Date of Patent: Aug. 13, 2013

(54) METHOD FOR MEASURING PHYSIOLOGICALLY ACTIVE SUBSTANCE OF BIOLOGICAL ORIGIN, PROGRAM FOR IMPLEMENTING THE SAME, AND APPARATUS FOR MEASURING PHYSIOLOGICALLY ACTIVE SUBSTANCE OF BIOLOGICAL ORIGIN

(75) Inventors: Katsumi Yabusaki, Hamamatsu (JP); Takuya Hara, Hamamatsu (JP); Yuka Sugiura, Hamamatsu (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 0 days.

(21) Appl. No.: 13/256,427

(22) PCT Filed: Mar. 12, 2010

(86) PCT No.: PCT/JP2010/054252
§ 371 (c)(1),
(2), (4) Date: Sep. 13, 2011

(87) PCT Pub. No.: WO2010/104180
PCT Pub. Date: Sep. 16, 2010

(65) Prior Publication Data
US 2012/0003745 A1    Jan. 5, 2012

(30) Foreign Application Priority Data

Mar. 13, 2009 (JP) ................. 2009-061737
Dec. 2, 2009 (JP) ................. 2009-274890

(51) Int. Cl.
*G01N 33/92* (2006.01)
*G01N 33/48* (2006.01)
*G01N 21/47* (2006.01)
*G01N 21/64* (2006.01)
*G01N 21/76* (2006.01)
*G01N 21/82* (2006.01)

(52) U.S. Cl.
USPC .................. 436/71; 436/63; 436/69; 436/94; 436/164; 436/172; 422/73; 422/82.05; 422/82.08; 422/82.09; 73/64.41; 73/64.43; 356/317; 356/337; 356/432; 356/433; 356/441; 356/442

(58) Field of Classification Search
USPC ................. 436/63, 69, 71, 94, 164, 171, 172; 422/68.1, 73, 82.05, 82.08, 82.09; 73/64.41, 73/64.43; 356/300, 317, 337, 432, 433, 441, 356/442
See application file for complete search history.

(56) References Cited

U.S. PATENT DOCUMENTS 4,221,866 A * 9/1980 Cotter ............................. 435/4
4,740,460 A * 4/1988 Sakata et al. .................... 435/18

(Continued)

FOREIGN PATENT DOCUMENTS

CN       1815235 A     8/2006
EP       0180905 A2    5/1986

(Continued)

OTHER PUBLICATIONS

International Search Report dated Apr. 27, 2010 issued to international application No. PCT/JP2010/054252.

(Continued)

*Primary Examiner* — Maureen Wallenhorst
(74) *Attorney, Agent, or Firm* — Knobbe Martens Olson & Bear LLP

(57) ABSTRACT

When assessing the start time of the limulus reaction between biogenous biologically active substances and LAL and using the reaction start time to determine the concentration of the biogenous biologically active substances, in order to exclude the influence of progressive changes which occur regardless of the conditions of the limulus reaction, the strength of transmitted light or scattered light in the liquid mixture of the measurement sample and LAL is detected, the variation (delta) in the transmittance or number of gel particles is acquired at set intervals, and the time when the variation (delta) crosses a threshold value is taken as the reaction start time. Furthermore, the time intervals when acquiring the abovementioned delta are not uniform, and either change over time from the start of measurement as defined by a time function, or multiple sequences with differing time intervals are prepared in advance.

29 Claims, 22 Drawing Sheets

(56) References Cited

U.S. PATENT DOCUMENTS

| | | | |
|---|---|---|---|
| 5,310,657 A * | 5/1994 | Berzofsky | 435/34 |
| 8,211,651 B2 * | 7/2012 | Yabusaki | 435/7.1 |
| 2011/0013185 A1 * | 1/2011 | Obata | 356/338 |
| 2011/0091902 A1 * | 4/2011 | Yabusaki | 435/7.1 |
| 2011/0124036 A1 * | 5/2011 | Yabusaki | 435/29 |
| 2012/0015377 A1 * | 1/2012 | Hirono | 435/7.21 |
| 2012/0040385 A1 * | 2/2012 | Yabusaki | 435/13 |

FOREIGN PATENT DOCUMENTS

| | | |
|---|---|---|
| EP | 0426395 A1 | 5/1991 |
| EP | 0 731 354 | 9/1996 |
| EP | 2 081 024 | 7/2009 |
| EP | 2397857 A1 | 12/2011 |
| JP | 59-042451 | 3/1984 |
| JP | 61-159162 | 7/1986 |
| JP | 10-293129 | 11/1998 |
| JP | 2004-061314 | 2/2004 |
| JP | 2004-212120 | 7/2004 |
| JP | 2009-150723 | 7/2009 |
| WO | WO 95/14932 | 6/1995 |
| WO | WO 2006/076617 A2 | 7/2006 |
| WO | WO 2008/038329 | 4/2008 |

OTHER PUBLICATIONS

Extended European search report issued in corresponding European Patent Application No. 10750931.7 on Mar. 15, 2013.

Ditter et al., "Quantitative Determination of Endotoxin/Automated limulus amoebocyte lysate microtiter test with determination of sample-related interferences," Arzneim.-Forsch./Drug Res. 33, pp. 681-687 (1983), with English summary.

Jorgensen et al., "Automation of the *Limulus* Amoebocyte Lysate Test by Using the Abbott MS-2 Microbiology System," Applied and Environmental Microbiology, vol. 41(6), pp. 1316-1320 (Jun. 1981).

Lindsay et al., "Single-step, Chromogenic *Limulus* Amebocyte Lysate Assay for Endotoxin," Journal of Clinical Microbiology, vol. 27(5), pp. 947-951 (May 1989).

* cited by examiner

METHOD FOR MEASURING PHYSIOLOGICALLY ACTIVE SUBSTANCE OF BIOLOGICAL ORIGIN, PROGRAM FOR IMPLEMENTING THE SAME, AND APPARATUS FOR MEASURING PHYSIOLOGICALLY ACTIVE SUBSTANCE OF BIOLOGICAL ORIGIN

CROSS-REFERENCE TO RELATED APPLICATIONS

This application is the U.S. National Phase under 35 U.S.C. §371 of International Application PCT/JP2010/054252, filed Mar. 12, 2010, which was published in a non-English language, which claims priority to JP Application No. 2009-061737, filed Mar. 13, 2009 and JP Application No. 2009-274890 Dec. 2, 2009.

TECHNICAL FIELD

The present invention relates to a measurement method and a measurement apparatus for detecting a physiologically active substance of biological origin in a sample that contains such a physiologically active substance having a characteristic feature of gelation caused by a reaction with LAL, such as endotoxin and β-D-glucan, or for measuring the concentration of the physiologically active substance.

BACKGROUND ART

Endotoxin is a lipopolysaccharide present in a cell wall of a Gram-negative bacterium and is the most typical pyrogen. If a transfusion, a medicine for injection, blood or the like contaminated with the endotoxin enters into a human body, the endotoxin may induce severe side effects such as fever and shock. Therefore, it is required to manage the above-mentioned medicines so that they are not contaminated with endotoxin.

By the way, a hemocyte extract of limulus (hereinafter, also referred to as "limulus amoebocyte lysate (LAL)") contains serine protease that is an enzyme activated by endotoxin. When LAL reacts with endotoxin, a coagulogen present in LAL is hydrolyzed into a coagulin by an enzyme cascade by the serine protease activated according to the amount of endotoxin, and the coagulin is associated to form an insoluble gel. With the use of this property of LAL, it is possible to detect endotoxin with a high sensitivity.

Furthermore, β-D-glucan is a polysaccharide that constitutes a cell membrane characteristic of a fungus. Measurement of β-D-glucan is effective, for example, for screening of infectious diseases due to a variety of fungi including not only fungi that are frequently observed in general clinical practices, such as Candida, Aspergillus, and Cryptococcus, but also rare fungi.

Also in the measurement of β-D-glucan, by using the property of the limulus amoebocyte lysate to coagulate (coagulate to form a gel) by β-D-glucan, the β-D-glucan can be detected with a high sensitivity.

As a method for detecting the presence of or measuring the concentration of a physiologically active substance of biological origin (hereinafter, also referred to as a predetermined physiologically active substance) such as endotoxin and β-D-glucan by a limulus hemocyte extract, there is a turbidimetric method in which a liquid mixture of a sample for detection or concentration measurement of a predetermined physiologically active substance (hereinafter, simply referred to as a "measurement of predetermined physiologically active substance") and LAL is left standing and the turbidity of the sample due to the gel formation by a reaction between LAL and the predetermined physiologically active substance is measured over time and analyzed.

In the case of measuring the predetermined physiologically active substance with the above turbidimetric method, a liquid mixture of the measurement sample and the LAL is generated in a dry-heat sterilized measurement glass cell. Then, the gelation of the liquid mixture is optically measured from the outside. However, the turbidimetric method may take a very long time for gelation of LAL particularly in a sample with a low concentration of the predetermined physiologically active substance. Thus, an method which is capable of measuring the predetermined physiologically active substance within a short time has been desired.

In contrast, laser light scattering particle counting method has been proposed. In the laser light scattering particle counting method, a liquid mixture of a measurement sample and LAL is stirred using, for example, a magnetic stirring bar to generate fine gel particles and the presence of the predetermined physiologically active substance in the sample can be determined within a short time from the intensity of a laser light scattered by gel particles or the intensity of light passing through the liquid mixture (hereinafter, this method is also simply referred to as a light scattering method). On the other hand, a stirring turbidimetric method has been also proposed. This method is one form of the turbidimetric method, where a reaction is accelerated by stirring a measurement sample to unify the state of gelation in the liquid mixture. These methods are different in that both the turbidimetric method and the stirring turbidimetric method detect an optical transmittance, while the light scattering method detects generated particles. However, the determination in any of these methods is based on a threshold method that counts a time until the intensity of light transmitted from the liquid mixture or the number of particles calculated from the intensity or the number of peaks of scattered light exceeds a threshold.

Furthermore, there is a method in which a synthetic substrate for clotting enzyme added is previously placed in a sample and a phenomenon of coloring, fluorescence generation, or light generation of the synthetic substrate decomposed by the clotting enzyme is then determined. The method using coloring has been widely used as a colorimetric method and as one of important measurement procedures in a quantitative method of the predetermined physiologically active substance.

Among the above measurement methods, immediately after initiation of the measurement, a phenomenon in which a decrease in intensity of transmitted light is observed in the turbidimetric method and the stirring turbidimetric method, and a phenomenon in which an increase in intensity or the number of peaks of scattered light is observed in the light scattering method, without depending on the reaction of LAL (hereinafter, also referred to as a limulus reaction) with the predetermined physiologically active substance (hereinafter, this phenomenon is also referred to as progressive decrease/increase). This progressive decrease/increase affects a time until the intensity of transmitted light or the number of particles calculated from the intensity or the number of peaks of scattered light exceeds a threshold in the above measurement methods. Therefore, a decrease in measurement accuracy of the above measurement methods may occur. In the above measurement method, the lower the concentration of the predetermined physiologically active substance, the longer the measurement time until the intensity of transmitted light, or the number of particles obtained from the intensity or the number of peaks of scattered light exceeds a threshold. Thus, the lower the concentration of the predetermined physiologically active substance, the more the measurement tends to be affected by the progressive decrease/increase. In some cases, therefore, reaction-starting times, from which gelation or aggregation has started, have not been evaluated correctly.

As described above, a threshold method, a differentiation method, and the like have been used as means for determining gelation or coloring. The threshold method defines a reaction-starting time as a time point at which a physical quantity to be varied due to gelation or coloring becomes not less than a predetermined threshold set in advance or a time point at which it exceeds the threshold (hereinafter, simply referred to as a threshold-passing time point). The differentiation method is based on the degree of variation in optical transmittance or absorbance in a given period of time. It has been known that, when the threshold method is used, the relationship between the amount of a predetermined physiologically active substance in a sample and the reaction-starting time becomes a linear relationship with a negative slope in double logarithm. In addition, a time-varying curve of a physical quantity, such as optical transmittance or absorbance, to be varied due to gelation or coloring can be approximated to a logistic curve. Therefore, a very slow change is observed when it reacts with the predetermined physiologically active substance of a low concentration. In contrast, a steep change is observed when it reacts with the predetermined physiologically active substance of a high concentration. Therefore, when the same threshold is applied to both the reactions to determine a reaction-starting time, the threshold method has an inconvenience in that a measurement time for a low-concentration sample is prolonged.

On the other hand, in the differentiation method that calculates a variation in optical transmittance or absorbance, these variations and the concentration of the predetermined physiologically active substance subjected to the reaction linearly correlate with each other. However, the linear relationship is only limited to within a narrow range of concentrations. Thus, the measurement cannot be simultaneously performed at high and low concentrations.

In order to solve these problems, an area method using an area of time curve of optical transmittance or absorbance has been proposed. The area method records an area value of each time and determines a time point when the value becomes a predetermined threshold or more or exceeds the threshold as a reaction-starting time (detection time) of the predetermined physiologically active substance. As described above, however, "progressive decrease/increase", in which optical transmittance and absorbance are actually changed at a constant rate independently of the LAL reaction, may be observed. FIG. 21 is a diagram illustrating an exemplary variation in optical transmittance over time by an endotoxin reaction. During the period of about 18 minutes from the start of the measurement, it is found that progressive-decreasing phenomenon occurs and optical transmittance linearly decreases. In such a case, the area method causes a linear increase in area value independently of the LAL reaction. Thus, in some cases, the predetermined physiologically active substance has not been correctly measured.

CITATION LIST

Patent Document

Patent document 1: Japanese Patent Application Laid-Open No. 2004-061314
Patent Document 2: Japanese Patent Application Laid-Open No. 10-293129
Patent document 3: PCT International Publication No. WO 2008/038329
Patent document 4: Japanese Patent Application Laid-Open No. 2009-150723

SUMMARY OF THE INVENTION

Problem to be Solved by the Invention

The present invention has been made in consideration of the aforementioned problems, and an object thereof is to provide a measurement method capable of more increasing measurement accuracy in detection or concentration measurement of a physiologically active substance of biological origin and to provide a measurement apparatus using the measurement method.

Means for Solving the Problem

In the present invention, in order to exclude an influence of progressive decrease/increase in the measurement of the above-mentioned predetermined physiologically active substance, the most characteristic feature is to continuously acquire difference values of physical quantity, which varies with the reaction between a measurement sample and LAL in a liquid mixture of the measurement sample and LAL, and the time when the difference value becomes not less than the threshold or exceeds the threshold is taken as a reaction-starting time.

More specifically, a method for measuring a physiologically active substance of biological origin, includes:

mixing a limulus amoebocyte lysate, LAL, with a sample containing a predetermined physiologically active substance of biological origin;

acquiring, after the mixing, a predetermined physical quantity, which varies due to the reaction between LAL and the physiologically active substance, continuously as a detected value;

defining one acquisition time as a reaction-starting time when a difference between a detected value at the one acquisition time and a detected value at a previous acquisition time before a predetermined time interval from the one acquisition time or an absolute value of the difference becomes not less than or exceeds the threshold; and detecting the physiologically active substance in the sample or measuring the concentration of the physiologically active substance, based on the reaction-starting time.

In the present invention, in order to exclude an influence of progressive decrease/increase in the measurement of the above-mentioned predetermined physiologically active substance, from the intensity or the number of peaks of transmitted light or scattered light from the liquid mixture of the measurement sample and LAL, the variation (difference) in the transmittance or number of gel particles is acquired at set intervals, and the time when the variation (difference) exceeds a threshold may be taken as the reaction-starting time.

In this case, more specifically, in the method for measuring a physiologically active substance of biological origin, the physiologically active substance of biological origin in the sample is reacted with a limulus amoebocyte lysate, LAL to detect the physiologically active substance in the sample or measure the concentration of the physiologically active substance, after mixing the sample and LAL, light is incident on a liquid mixture of the sample and LAL, among the incident light, the intensity of light having passed through the liquid mixture or light scattered on the liquid mixture is acquired, a predetermined physical quantity which is acquired by the intensity of the acquired light at an acquisition time set up with a predetermined time interval, is defined as a detected value, and a reaction-starting time is defined as a time at which a difference between the detected value at the one acquisition time and a detected value at a previous acquisition time or the absolute value of the difference exceeds the threshold, and the physiologically active substance in the sample is detected or the concentration of the physiologically active substance is measured, based on the reaction-starting time.

Here, it is found that, when the above-mentioned progressive decrease/increase occurs, the intensity of transmitted light or the intensity or the number of peaks of scattered light is unrelated to the concentration of a predetermined physiologically active substance, but almost linearly varies with time. On the other hand, in the present invention, the intensity of the transmitted light or scattered light from the liquid mixture is acquired. Then, a detected value is defined as the intensity of light acquired at an acquisition time set by a predetermined time interval or defined as a value obtained by modifying the acquired intensity of light depending on an object at the acquisition time, and a reaction-starting time is defined as a time at which a difference between the detected value at one acquisition time and a detected value at a previous acquisition time (i.e., amount of variation in detected value at set intervals) or the absolute value of the difference exceeds the threshold. Therefore, it becomes possible to cancel the influence of progressive decrease/increase on the measurement of a predetermined physiologically active substance.

According to the present invention, therefore, a starting time for the reaction of the predetermined physiologically active substance in a sample with LAL can be determined with higher accuracy. As a result, the detection of a predetermined physiologically active substance or the measurement of the concentration thereof can be performed with higher accuracy.

In the present invention, furthermore, the acquired light intensity is the intensity of light having passed through the liquid mixture. The detected value is a transmittance of the liquid mixture expressed in percentage. The predetermined time interval may be set to about 2 minutes. The reaction-starting time may be a time at which the absolute value of the difference between the transmittance at the one acquisition time and the transmittance obtained at the previous acquisition time exceeds 1.

This case relates to a turbidimetric method where light passing through a liquid mixture is acquired among light rays incident on the liquid mixture of a predetermined physiologically active substance and LAL and the transmittance of the transmitted light is then acquired. In the turbidimetric method, as mentioned above, the liquid mixture becomes turbid due to the reaction between the predetermined physiologically active substance and LAL. As a result, the transmittance of the liquid mixture decreases over time. Here, the shape of a decreasing curve of transmittance in turbidimetric method varies depending on the concentration of the predetermined physiologically active substance. For example, when the concentration of the predetermined physiologically active substance is high, the transmittance falls steeply. On the other hand, when the concentration of the predetermined physiologically active substance is low, the transmittance falls gently.

When the interval of acquiring detected values is set longer in the case of a high concentration of a predetermined physiologically active substance and a steep decrease in transmittance, a sufficient number of data cannot be acquired due to an excessively large degree of a decrease in each detected value at a time. As result, high-precision measurement becomes difficult. On the other hand, when a detection-value acquisition interval is set too short in the case of a low concentration of a predetermined physiologically active substance and a moderate decrease in transmittance, the difference cannot be detected with sufficient accuracy due to an excessively small degree of a decrease in each detected value at a time. According to the present invention, therefore, it is preferable to adjust time intervals for acquiring detected values depending on the concentration of a predetermined physiologically active substance in a sample to be provided as a measuring object.

On the other hand, as a result of an intensive study of the inventors, it has become clear that a decreasing curve of transmittance can be obtained with high accuracy in a broader concentration range of a predetermined physiologically active substance in the present invention in the case where a detection-value (transmittance) acquisition interval is set to about 2 minutes when a transmittance is expressed in percentage. In this case, furthermore, it is found that the concentration of a predetermined physiologically active substance can be measured at high accuracy in the case where a reaction-starting time is defined as a time at which the decrement of transmittance for 2 minutes exceeds 1%.

Therefore, in the present invention, a transmittance is calculated by acquiring transmitted light from a liquid mixture of a predetermined physiologically active substance and LAL, a predetermined time interval is set to about 2 minutes in the case of acquiring a difference (variation) in transmittance at a predetermined time interval, and a reaction-starting time is defined as a time at which the decrement of transmittance for 2 minutes exceeds 1%. Therefore, the detection of predetermined physiologically active substance or the measurement of the concentration thereof in a wider range of samples can be performed with higher accuracy.

In the present invention, furthermore, the intensity of the acquired light is the intensity of light scattered by the liquid mixture. The detected value is the number of particles that scatter the light incident on the liquid mixture and is derived based on the predetermined number of peaks of the intensity of the scattered light. Thus, the predetermined time interval may be set to about 100 seconds, and the reaction-starting time may be defined as a time at which a difference between the number of particles at the one acquisition time and the number of particles at the previous acquisition time exceeds 200.

This case relates to a light scattering method where, among light rays incident on a liquid mixture of a predetermined physiologically active substance and LAL, light scattered from the liquid mixture is obtained, and the number of particles (gel) in the liquid mixture is acquired from the number of peaks (satisfying predetermined conditions for improvement of measurement accuracy) in the scattered light. In the light scattering method, as mentioned above, stirring the liquid mixture in reaction between the predetermined physiologically active substance and LAL generates gel particles in the liquid mixture. The size and number of the gel particles increase as the reaction proceeds. Thus, the number of peaks observed in the light scattered from the liquid mixture increases as the reaction proceeds.

In addition, the profile of an increasing curve representing the number of peaks of scattered light in the light scattering method varies depending on the concentration of the predetermined physiologically active substance. For example, the number of peaks increases steeply in the case of high concentration of the predetermined physiologically active substance, while the number of peaks increases gradually in the case of low concentration of the predetermined physiologically active substance. Therefore, as is the case with the turbidimetric method, it is preferable for the light scattering method to adjust time intervals for acquiring detected values depending on the concentration of a predetermined physiologically active substance in a sample to be provided as a measuring object.

In contrast, as a result of an intensive study of the inventors, in the light scattering method, it has become clear that an increasing curve of the number of peaks can be obtained with higher accuracy in a broader concentration range of a predetermined physiologically active substance in the case where a detection-value (number of scattered particles) acquisition interval is set to about 100 seconds. In this case, furthermore, it is found that the concentration of a predetermined physiologically active substance can be measured at high accuracy in the case where a reaction-starting time is defined as a time at which the increment of the number of scattered particles for 100 seconds exceeds 200.

Therefore, in the present invention, light scattered from a liquid mixture of a predetermined physiologically active substance and LAL is acquired and the number of scattered particles is then detected, a predetermined time interval is set to about 100 seconds when a difference (variation) in the number of scattered particles at predetermined time intervals is acquired, and a reaction-starting time is defined as a time at which the increment of the number of scattered particles for 100 seconds exceeds 200. Therefore, the detection of a predetermined physiologically active substance or the measurement of the concentration thereof can be performed on a wider range of samples with higher accuracy.

First, as described above, the present invention has proposed a difference method, which will described later, where the value of difference in optical transmittance or the number of light scattering particles between two points at predetermined time intervals is recorded at each time, and a detection time is defined as a time at which the value passes a previously determined threshold. Unlike the differentiation method, in the difference method, the variation itself is not associated with the concentration of the predetermined physiologically active substance. The difference method associates a time required for exceeding a threshold and the concentration of a predetermined physiologically active substance. Therefore, the difference method overcomes an inconvenience of narrow measurable concentration range as observed in the differentiation method. Furthermore, even in the case where there is a linear change in optical transmittance or absorbance, which may occur regardless of reaction with LAL, this change becomes constant by taking a difference value. Thus, the change is easily removable and an improvement in measurement accuracy can be attained.

However, in the difference method, when measuring a predetermined physiologically active substance in low concentration with gradual transition in a change curve, it becomes difficult to acquire a large difference value required for the measurement. Thus, the measurement may become difficult. Therefore, it has been strongly desired to establish a high-accuracy measurement method that is not influenced by a change in optical transmittance, absorbance, or the like independent of reaction with LAL, while allowing the measurement of a wide concentration range of a predetermined physiologically active substance.

In the present invention, therefore, a method for measuring a physiologically active substance of biological origin with reference to a time when a physical quantity to be varied due to a reaction between a limulus amoebocyte lysate, LAL, and the physiologically active substance of biological origin exceeds a threshold may employ the following means for the purpose of offering a technology that can obtain higher measurement accuracy.

In this case, the present invention relates to a difference method where the value of a difference in physical quantity that varies with a reaction between a sample containing a predetermined physiologically active substance and LAL at two time points with predetermined intervals is continuously acquired, and a reaction-starting time is defined as a time at which the value exceeds a previously defined threshold. Furthermore, the most characteristic feature of the present invention is that the time interval between two time points is not made constant and variable with times so that a realistic reaction-starting time is obtained even in the case of measurement of a low-concentration sample.

More specifically, a method for measuring a physiologically active substance of biological origin includes: mixing a limulus amoebocyte lysate, LAL, with a sample containing a predetermined physiologically active substance of biological origin; acquiring, after the mixing, a predetermined physical quantity, which varies due to the reaction between LAL and the physiologically active substance, continuously as a detected value; setting one acquisition time as a reaction-starting time when a difference between a detected value at the one acquisition time and a detected value at a previous acquisition time before a predetermined time interval from the one acquisition time or the absolute value of the difference becomes not less than or exceeds the threshold; and detecting the physiologically active substance in the sample or measuring the concentration thereof based on the reaction-starting time, wherein the predetermined time interval is changed with reference to the one acquisition time.

That is, in the measurement of a predetermined physiologically active substance, in the case where progressive increase/decrease, which is changed independently of the reaction between LAL and the predetermined physiologically active substance, is observed, it is thought that the influence of the progressive increase/decrease is removed and an increase in accuracy of the measurement of a predetermined physiologically active substance can be obtained by taking the difference of the detected value at constant time intervals. However, particularly in the measurement of a low-concentration predetermined physiologically active substance, the variation of the detected value itself is small. Thus, a sufficient difference value cannot be acquired when the time interval at the time of taking a difference is narrow. As a result, there is a case where the measurement of a predetermined physiologically active substance becomes difficult.

In contrast, in the present invention, the time interval for taking a difference is changed with reference to the acquisition time of a detected value. In other words, when a difference value is extremely small, which has been hardly measured until now, the time interval for taking a difference is set long to make the difference exceed a threshold at least at a realistic time. Thus, even if the concentration of a predetermined physiologically active substance in the measurement sample is either high or low, it is possible to carry out the measurement of a predetermined physical active substance at high accuracy.

Here, examples of the above physical quantity include optical intensity, such as optical transmittance, absorbance, scattered light intensity, the number of light scattering particles, fluorescence intensity, and chemiluminescence intensity, or electrical engineering intensity, such as the viscosity and electrical conductivity of a sample.

In the present invention, furthermore, light is incident on the liquid mixture of the LAL and the sample and, among the incident light, the intensity of light having passed through the liquid mixture or light scattered on the liquid mixture may be continuously detected. Then, any one of optical transmittance, absorbance, scattered light intensity, the number of light scattering particles, fluorescence intensity, and chemiluminescence intensity, which are acquired from the intensity of the light continuously detected, may be used as a detected value.

Therefore, it becomes possible to continuously acquire physical quantity that varies due to the reaction between LAL and the physiologically active substance after mixing the LAL and the physiologically active substance by a noncontact method. Thus, the measurement of a predetermined physiologically active substance can be more easily performed with high accuracy.

In the present invention, furthermore, the later the one acquisition time becomes, the longer the predetermined time interval may be set.

In other words, the time interval for acquiring a difference is defined by a time function of an elapsed time from a measurement start. Therefore, in the case where the concentration of a predetermined physiologically active substance is low, the difference between the detected values acquired at two acquisition times is small, and the difference value is still not more than a threshold, it is possible to relatively increase a difference value by extending the time interval. As a result, even if the concentration of the predetermined physiologically active substance is low, the difference value can exceed the threshold easier. Thus, it is possible to obtain a measurement start time in a realistic measurement time.

In addition, the present invention may include a plurality of series each having the predetermined time interval set constant, where the predetermined time intervals of the respective series are different from one another, and may change the series to be used with reference to the one acquisition time.

Here, for example, the present invention may include a series with a predetermined time interval of 1 minute, a series with a predetermined time interval of 6 minutes, and a series with a predetermined time interval of 30 minutes. Then, the series of acquisition times to be used is changed with reference to the acquisition time of the physical quantity. For example, a series with long time intervals may be used in the case of a low concentration of a predetermined physiologically active substance, a small difference between the detected values acquired at two acquisition time points, and the difference value being still not more than a threshold. Then, it is possible to relatively increase a difference value. As a result, even if the concentration of the predetermined physiologically active substance is low, the difference value can exceed the threshold. Thus, it is possible to obtain a measurement start time in a realistic measurement time.

In the present invention, furthermore, the series to be used may be one in which a difference between a detected value at the one acquisition time and a detected value at a previous acquisition time before a predetermined time interval from the one acquisition time or the absolute value of the difference is the highest.

In other words, at each time of acquiring physical quantity, a series with the maximum difference value of the detected value is selected among a plurality of series and a difference value in this series is compared with the threshold. Thus, it is possible to always make a comparison between the maximum difference value and the threshold. Therefore, a time until the difference value exceeds the threshold can be shortened as much as possible. As a result, it becomes possible to measure the predetermined physiologically active substance more efficiently. In addition, an inconvenience in that the difference value does not exceed the threshold and the measurement becomes impossible can be eliminated.

In the present invention, furthermore, a plurality of differences or the absolute values thereof, in which each difference is of between a detected value at the one acquisition time and a detected value at a previous acquisition time before a predetermined time interval from the one acquisition time, is acquired at different acquisition times. The resulting differences are lined up in descending order and the value at the predetermined rank is defined as a reference difference value, and the reference difference value is subtracted from the difference or the absolute value thereof. When the resulting value is equal to or higher than the threshold or exceeds the threshold, the one acquisition time may serve as a reaction-starting time.

Here, when the progressive decrease/increase occurs in the detected value of the physical quantity after starting the measurement, the difference or the absolute value thereof obtained in early stage after starting the measurement is subtracted from a difference between a detected value at the one acquisition time and a detected value at a previous acquisition time before a predetermined time interval from the one acquisition time or the absolute value thereof. Thus, it is possible to reduce an influence of the progressive decrease/increase on the measurement.

However, when a detected value, a difference from the detected value, or an absolute value thereof is small, a value to be subtracted in itself is hardly obtained with accuracy. In some cases, therefore, it is difficult to eliminate an influence of progressive decrease/increase with high accuracy. In the present invention, therefore, a plurality of differences or the absolute values thereof, in which each difference is of between a detected value at the one acquisition time and a detected value at a previous acquisition time before a predetermined time interval from the one acquisition time, is acquired at different acquisition times in advance. The resulting differences or the absolute values thereof are lined up in descending order and the value at the predetermined rank is defined as a reference difference value. The reference difference value is subtracted from the difference or the absolute value thereof. Then, the value obtained by the subtraction and the threshold are compared with each other.

For example, the above difference or the absolute value thereof obtained in the past may be rearranged in descending order. Among lowest five data, the third lowest value may be used as a reference difference value. In this case, even when a detected value, a difference from the detected value, or an absolute value thereof is small, the reliability of a value to be subtracted can be raised. Thus, it is possible to reduce an influence of progressive decrease/increase with higher accuracy.

In the present invention, furthermore, the physiologically active substance of biological origin may be endotoxin or $\beta$-D-glucan.

Therefore, the detection or concentration measurement of endotoxin, which is the most typical pyrogen, can be performed more correctly. Infusion solutions, injection agents, the blood, or the like, which are contaminated with endotoxin, can be prevented from being introduced into the human body and causing side effects. Similarly, detection or concentration measurement of $\beta$-D-glucan can be also performed more correctly. Thus, it is possible to screen fungal infections of a wide variety of fungi including not only those commonly found in clinical sites, such as Candida, Aspergillus, and Cryptococcus, but also uncommon fungi.

Furthermore, the present invention may be an apparatus for measuring a physiologically active substance of biological origin including: a liquid mixture retaining means for retaining liquid mixture of a sample containing a predetermined physiologically active substance of biological origin and a limulus amoebocyte lysate, LAL, while allowing light to be incident on the liquid mixture and for promoting a reaction in the liquid mixture; a stirring means for stirring the liquid mixture in the liquid mixture retaining means; a light incidence means for entering light into the liquid mixture in the liquid mixture retaining means; a light receiving means for receiving transmitted light or scattered light of the incident light from the liquid mixture and converting the transmitted light or the scattered light into an electric signal; a determining means for determining a reaction-starting time between the physiologically active substance and LAL in the sample from the electric signal converted in the light receiving means; and a deriving means for deriving an existence or concentration of the physiologically active substance in the sample with reference to a relationship set in advance between the reaction-starting time and the concentration of the physiologically active substance, wherein the determining means determines a reaction-starting time as a time at which a difference between a detected signal value at one acquisition time among acquisition times set at predetermined time intervals, where a signal obtained by subjecting the electric signal to a predetermined calculation or the electric signal itself is used as a detected signal value, and a detected signal value at a previous acquisition time or an absolute value of the difference exceeds a threshold.

The apparatus for measuring a predetermined physiologically active substance of biological origin of the present invention receives transmitted light or scattered light from a liquid mixture of a predetermined physiologically active substance and LAL by the light receiving means and converts the light into an electric signal. Then, a reaction-starting time in the liquid mixture is determined from the converted electric signal by the determining means. The determining means acquires detected signal values at predetermined time intervals based on the obtained electric signals, and determines a reaction-starting time as a time at which a variation in detected signal values at predetermined intervals exceeds a threshold.

According to the measurement apparatus of the present invention, it becomes possible to automatically cancel the influence of progressive decrease/increase on the measurement of a predetermined physiologically active substance. Therefore, the detection or concentration measurement of a predetermined physiologically active substance can be performed with higher accuracy.

At this time, furthermore, when the detected signal value is the transmittance of the liquid mixture represented in terms of percentage, a predetermined time interval may be set to about two minutes and the threshold may be set to 1. Furthermore, when the detected signal value is the number of particles that scatter the light incident on the liquid mixture, a predetermined time interval may be set to about 100 seconds and the threshold may be set to 200. Thus, it is possible to acquire higher measurement accuracy and to target the concentrations of wider variety of predetermined physiologically active substances.

In the apparatus for measuring a predetermined physiologically active substance of biological origin of the present invention, a predetermined time interval and/or a threshold may be variable. Then, an acquisition time interval of a detected signal value and a threshold for determining a reaction-starting time can be optimized depending on an expected concentration of the predetermined physiologically active substance. Thus, higher measurement accuracy can be obtained with respect to the expected concentration.

The present invention may be an apparatus for measuring a physiologically active substance of biological origin including:

a liquid mixture retaining means for retaining a sample containing a predetermined physiologically active substance of biological origin and a limulus amoebocyte lysate, LAL, while allowing light to be incident on the liquid mixture and for promoting a reaction in the liquid mixture;

a stirring means for stirring the liquid mixture in the liquid mixture retaining means;

a light incidence means for entering light into the liquid mixture in the liquid mixture retaining means;

a light receiving means for receiving transmitted light or scattered light of the incident light from the liquid mixture and converting the transmitted light or the scattered light into an electric signal;

a determining means for determining a reaction-starting time between the physiologically active substance and LAL in the sample from the electric signal converted in the light receiving means; and a deriving means for deriving an existence or concentration of the physiologically active substance in the sample with reference to a relationship set in advance between the reaction-starting time and the concentration of the physiologically active substance, wherein the determining means determines a reaction-starting time as a time at which a difference between a detected signal value at one acquisition time among acquisition times set at predetermined time intervals, where a signal obtained by subjecting the electric signal to a predetermined calculation or the electric signal itself is used as a detected signal value, and a detected signal value at a previous acquisition time or an absolute value of the difference becomes not less than or exceeds a threshold.

In this apparatus for measuring a physiologically active substance of biological origin, furthermore, the determining means changes the predetermined time interval with reference to the one acquisition time.

In this case, the determining means may extend the predetermined time interval so that the later the one acquisition time becomes, the longer the predetermined time interval becomes.

Furthermore, the determining means may include a plurality of series each having the predetermined time interval set constant, where the predetermined time intervals of the respective series are different from one another, and may change the series to be used with reference to the one acquisition time.

Furthermore, the series to be used may be one in which a difference between a detected value at the one acquisition time and a detected value at a previous acquisition time before a predetermined time interval from the one acquisition time or the absolute value of the difference is the highest.

Furthermore, a plurality of differences or the absolute values thereof, in which each difference is of between a detected value at the one acquisition time and a detected value at a previous acquisition time before a predetermined time interval from the one acquisition time, is acquired at different acquisition times. The resulting differences are lined up in descending order and the value at the predetermined rank is defined as a reference difference value, and the reference difference value is subtracted from the difference or the absolute value thereof. Then, a reaction-starting time is determined as a time at which the resulting value of the subtraction becomes the threshold or more or exceeds the threshold.

Furthermore, the physiologically active substance of biological origin may be endotoxin or β-D-glucan.

Furthermore, the present invention may be a program for executing the above method for measuring a physiologically active substance of biological origin.

Here, the above means for attaining the objects of the present invention may be used in combination as much as possible.

Advantageous Effects of Invention

The present invention enables higher measurement accuracy to be achieved when using the reaction between LAL and physiologically active substance of biological origin such as endototin and β-D-glucan to detect or to measure the concentration of the physiologically active substance. Furthermore, higher measurement accuracy is obtainable in a method for measuring a physiologically active substance of biological origin with reference to a time when a physical quantity to be varied due to a reaction between the physiologically active substance of biological origin and LAL exceeds a threshold.

BEST MODE FOR CARRYING OUT THE INVENTION

Figure 22:
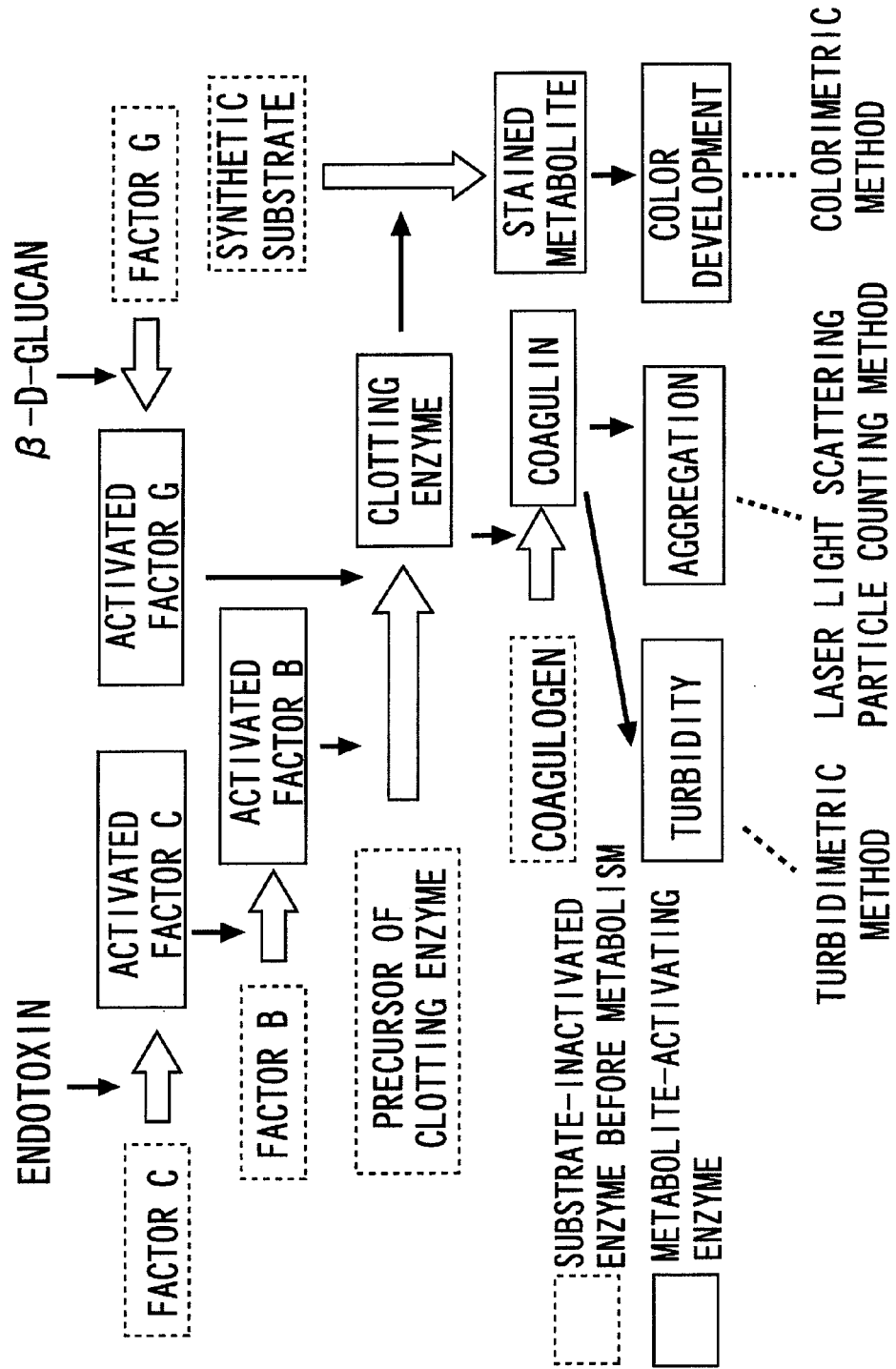
FIG. 22 is a schematic diagram illustrating a process where endotoxin or β-D-glucan causes LAL to gelate and methods for detecting the gelation.

The process of forming a gel by a reaction between LAL and endotoxin has been studied well. That is, as illustrated in FIG. 22, when endotoxin is bound to a serine protease, i.e., factor C in LAL, the factor C is activated to become activated factor C. The activated factor C hydrolyzes and activates another serine protease, i.e., factor B in LAL, and then the factor B is activated to become activated factor B. The activated factor B immediately hydrolyzes a precursor of clotting enzyme in LAL to form clotting enzyme, and further the clotting enzyme hydrolyzes a coagulogen in LAL to generate coagulin. Thus, the generated coagulin are then associated with each other to further form an insoluble gel, and the whole LAL is involved in the formation to turn into a gel.

In addition, similarly, when β-D-glucan is bound to factor G in LAL, the factor G is activated to become activated factor G. The activated factor G hydrolyzes a precursor of clotting enzyme in LAL to produce clotting enzyme. As a result, as is the case with the reaction between endotoxin and LAL, coagulin are generated, and the generated coagulin are associated with each other to further generate an insoluble gel.

The series of reactions as described above are similar to the process of forming a fibrin gel via serine proteases such as Christmas factor or thrombin present in mammals. Such enzyme cascade reactions have a very strong amplification effect because even a very small amount of an activation factor activates the subsequent cascade in a chain reaction. Therefore, according to a method of measuring a predetermined physiologically active substance using LAL, it is possible to detect a very small amount (sub-pg/mL order) of the predetermined physiologically active substance.

Reagents for quantifying the endotoxin and β-D-glucan, which can be used, may be a Limulus reagent containing a limulus hemocyte extract (LAL: Limulus amebocyte lysate) as a raw material, and a reagent prepared by adding a synthetic substrate, where either coloring intensity, fluorescence intensity, or chemiluminescence intensity is increased when it is hydrolyzed by a clotting enzyme, to the Limulus reagent. In some cases, for example, a mixture reagent of a recombinant of factor C (recombinant factor C) in a Limulus reagent and a synthetic substrate (irrespective of coloring, fluorescence, and chemiluminescence) may be used. Furthermore, a mixture reagent of a recombinant of factor G (recombinant factor G) in a Limulus reagent and a synthetic substrate (irrespective of coloring, fluorescence, and chemiluminescence) may be used.

Furthermore, various kinds of physical quantities may be considered to quantify endotoxin and β-D-glucan. The types of the reagents and the kinds of the measurement apparatus may be selected with reference to their physical quantities. Examples of the above physical quantity include the optical physical quantities, such as transmittance of a sample, turbidity, scattered light intensity, the number of light scattering particles, absorbance, fluorescence intensity, and chemiluminescence intensity, and the change of these optical physical quantities may be detected. Alternatively, a change in physical quantities such as the viscosity or electric conductivity of a sample with gelation may be detected. These physical quantities can be detected using optical apparatuses, such as a turbidimeter, an absorptiometer, a light scattering photometer, a laser light scattering particle counting apparatus, a fluorometer, and a photon counter, and dedicated measurement apparatuses to which these are applied. Furthermore, a viscosity meter and an eclectic conductivity meter and dedicated apparatuses to which these are applied may be also used.

Measurement methods, which are capable of quantifying predetermined physiologically active substance such as endotoxin and β-D-glucan, include various kinds of methods, such as a turbidimetric method, a stirring turbidimetric method, and a light scattering method as described above. As illustrated in FIG. 22, any of these measurement methods detects an aggregated product of coagulins generated by the enzyme cascade reaction of LAL, as the turbidity of a sample in the case of the former and as gel fine particles generated in the system in the case of the latter. Thus, a highly sensitive measurement can be performed.

The turbidimetric method has been evaluated as a convenient method at the work site in that no special reagent is required; a wide range of concentration of a predetermined physiologically active substance is measurable; and so on. On the other hand, however, the turbidimetric method has a disadvantage in that an extremely long time is required for measurement of a predetermined physiologically active substance in low concentration. This is because the turbidimetric method does not directly focus on the amount of coagulin produced, which is the final product of a protease cascade, but focuses on a process in which optical transmittance decreases as a gel is subsequently formed by association of coagulin.

In other words, gelation does not occur until the concentration of coagulin reaches a certain level or more, so that detection of a predetermined physiologically active substance in the turbidimetric method should wait for the formation of a gel. Therefore, the coagulin in necessary and sufficient concentration can be quickly generated and start gelation when the concentration of the predetermined physiologically active substance is high. Thus, the measurement time can be shortened. In contrast, when the concentration of the predetermined physiologically active substance is low, it takes much time to reach the concentration of coagulin necessary for gelation. Thus, the measurement time can be prolonged. In this respect, the stirring turbidimetric method intends to shorten the measurement time by facilitating a reaction between a predetermined physiologically active substance and LAL by stirring a liquid mixture thereof.

The light scattering method has improved points in comparison with the turbidimetric method. One of the improved points is to stir a sample and the other thereof is to detect particles by laser but not detect gelation. Thus, the light scattering method can significantly shorten the measurement time, compared with the turbidimetric method. The turbidimetric method, stirring turbidimetric method, and light scattering method are common in that a time at which a physical quantity exceeds a certain constant threshold is regarded as a reaction start point even though these methods focus on different physical quantities (this method is called a threshold method for convenience).

Here, a progressive decrease/increase phenomenon has been observed in any of the above measurement methods immediately after starting a measurement. That is, regardless of the state of a limulus reaction, it is observed that the turbidimetric method and the stirring turbidimetric method cause a decrease in optical transmittance of a liquid mixture and the light scattering method causes an increase in the number of gel particles in a liquid mixture. The reason for this phenomena has not been cleared. However, for example, it may occur when protein is denatured by a change in pH of a liquid mixture due to dissolution of carbon dioxide gas or the like into the liquid mixture.

In the stirring turbidimetric method and the light scattering method, a liquid mixture is stirred using a stirring bar in a measurement vessel. Thus, this stirring keeps the state of the limulus reaction constant or facilitates the reaction. It is also observed that the stirring may have a tendency of causing a progressive decrease/increase when the rotation axis of the stirring is inappropriate or the bottom surface of the measurement vessel has an inappropriate shape. The reason for this tendency is under intensive investigation.

When the concentration of the predetermined physiologically active substance in a measurement sample is high, before being influenced by a progressive decrease/increase, gelation of a liquid mixture proceeds and an aggregation determination is then completed. Therefore, there is comparatively a smaller risk that measurement accuracy falls due to the influence of progressive decrease/increase. However, when the concentration of a predetermined physiologically active substance in a measurement sample is low, a concentration measurement takes a long time. Therefore, the change curve of optical transmittance or the number of gel particles actually exceeds a threshold at a stage earlier than actually expected under the influence of progressive decrease/increase. Thus, the accuracy of a determination for reaction-starting time may be decreased.

In the detection or concentration measurement of a predetermined physiologically active substance, the present embodiment does not employ a procedure for determining a reaction-starting time based on a fact that the optical transmittance or the number of gel particles itself in a liquid mixture of a sample and LAL exceeds a threshold in preparation for the occurrence of a progressive decrease/increase phenomenon. The present embodiment employs a procedure for acquiring optical transmittance or the number of gel particles at a constant time interval and determining, as a reaction-starting time, a time at which the variation of optical transmittance or the number of gel particles at the time interval exceeds a threshold. The threshold is naturally different from one used in comparison with the turbidity or the number of gel particles. Thus, even if a progressive decrease/increase occurs, the influence thereof can be removed and the start time of a reaction between a predetermined physiologically active substance and LAL can be determined with higher accuracy. (This method is called a difference method for convenience).

Therefore, a time at which a sudden change in variation of turbidity or the number of gel particles in a liquid mixture occurs can be assessed. Thus, it is possible to increase measurement accuracy for a low-concentration sample as well as a high-concentration sample. Furthermore, according to this fact, it is possible to remove the influence of progressive decrease/increase by changing only a process for analyzing data obtained in measurement of a predetermined physiologically active substance.

Hereinafter, the details of embodiments of the present invention will be described. However, the present invention is not limited to the embodiments described below. Here, in the following embodiments, descriptions will be made with respect to cases where the predetermined physiologically active substance is endotoxin. However, the same may be also applicable to other cases where the predetermined physiologically active substance is β-D-glucan.

Here, targets for detection in measurement of endotoxin are different from one another in the above measurement methods, respectively. Each of the turbidimetric method and the stirring turbidimetric method detects the turbidity of a liquid mixture when the liquid mixture turns into a gel or an aggregate as a result of action of endotoxin on a LAL reagent. Therefore, the transmitted light of a liquid mixture is acquired and a start time of a reaction between endotoxin and LAL is then determined as a time at which the optical transmittance of the liquid mixture becomes lower than a previously defined threshold.

In each of the turbidimetric method and the stirring turbidimetric method, a moving average for 2 minutes is taken in order to remove the noise of detected value when there is a tendency for the optical transmittance of liquid mixture to decrease regardless of the conditions of the limulus reaction. Next, since data is unstable immediately after the measurement start, the optical transmittance after 2 minutes from the measurement start is defined as 100%. A difference of optical transmittance value (%) originally obtained every 10 seconds at a previously defined time interval $\Delta T$ is taken and a first time when a square value of the difference exceeds 1 continuously three times is employed as a reaction-starting time. The time interval $\Delta T$ of differences is preferably 1 to 5 minutes, and particularly about 2 minutes is preferred. In the case of a low-concentration sample, the variation of optical transmittance is small. Thus, it is preferable to set the time interval $\Delta T$ to 5 minutes. Here, the reason for squaring the difference of optical transmittance (%) at the time interval $\Delta T$ is to improve a resolution by increasing a change when the difference value becomes almost 1. Thus, the difference does not always need to be squared.

On the other hand, in the light scattering method, the process of the gelation or aggregation of a liquid mixture is observed in a manner similar to that of the turbidimetric method and the stirring turbidimetric method, except that light scattered by aggregated clusters (gel particles) in the liquid mixture is acquired. That is, the number of gel particles is increased by aggregation caused by mixing a sample, which is originally transparent and free of gel particles, with a Limulus reagent. An increase in the number of gel particles leads to an increase of frequency of peak generation in scattered light. Thus, the number of peaks in the scattered light can be acquired as the number of gel particles. Then, a threshold is set to an integrated value of the numbers of gel particles detected during a predetermined time period. Then, a time at which the number of detected particles exceeds the threshold is defined as a reaction-starting time.

When the tendency of an increase in the number of gel particles detected in the light scattering method regardless of the conditions of the limulus reaction is observed, a difference of detected values (the number of gel particles) at a certain time interval $\Delta T$, or the increasing number of particles, is acquired. For determining a reaction-starting time of the limulus reaction, a first time at which a difference between the numbers of gel particles exceeds a threshold of 200 continuously 10 times is defined as a reaction-starting time in consideration of noise influence. The time interval $\Delta T$ of differences is preferably 30 to 200 seconds, particularly preferably about 100 seconds so as to respond to a sample with a high endotoxin concentration.

In the above measurement, the time interval $\Delta T$ for detected value acquisition should be set to a comparatively large value when the concentration of endotoxin is low, while it should be set to a comparatively small value when the concentration of endotoxin is high. This is because the lower the concentration of endotoxin, the smaller the variation of the turbidity or the number of gel particles after mixing a sample with a LAL reagent. Thus, a sufficient time interval is required for ensuring a sufficiently large difference in detected values before and after the time interval $\Delta T$.

On the other hand, since a limulus reaction between endotoxin and LAL proceeds comparatively quickly, aggregation may begin during the set time interval $\Delta T$ when the concentration of endotoxin is high. Therefore, variations in detected values of the turbidity of a liquid mixture or the number of gel particles in the liquid mixture are sequentially detected. Then, it is roughly estimated whether the endotoxin concentration is low or high. The estimated value is used for changing the time interval $\Delta T$ for different cases to measure endotoxin concentration more accurately. Therefore, the above estimating method may be employed if needed.

Production Example 1

A stirring bar made of stainless steel (1 mm in diameter and 5 mm in length) was placed in a glass vessel (7 mm in outer diameter and 50 mm in length, hereinafter referred to as a cuvette). An opening of the cuvette was covered with a sheet of aluminum foil and 20 cuvettes were then collectively covered with a sheet of aluminum foil, followed by being subjected to heating at 250° C. for 3 hours to dry-heat the cuvette.

Consequently, endotoxin adhered on the cuvette are thermally decomposed and inactivated.

Example 1

Figure 1:
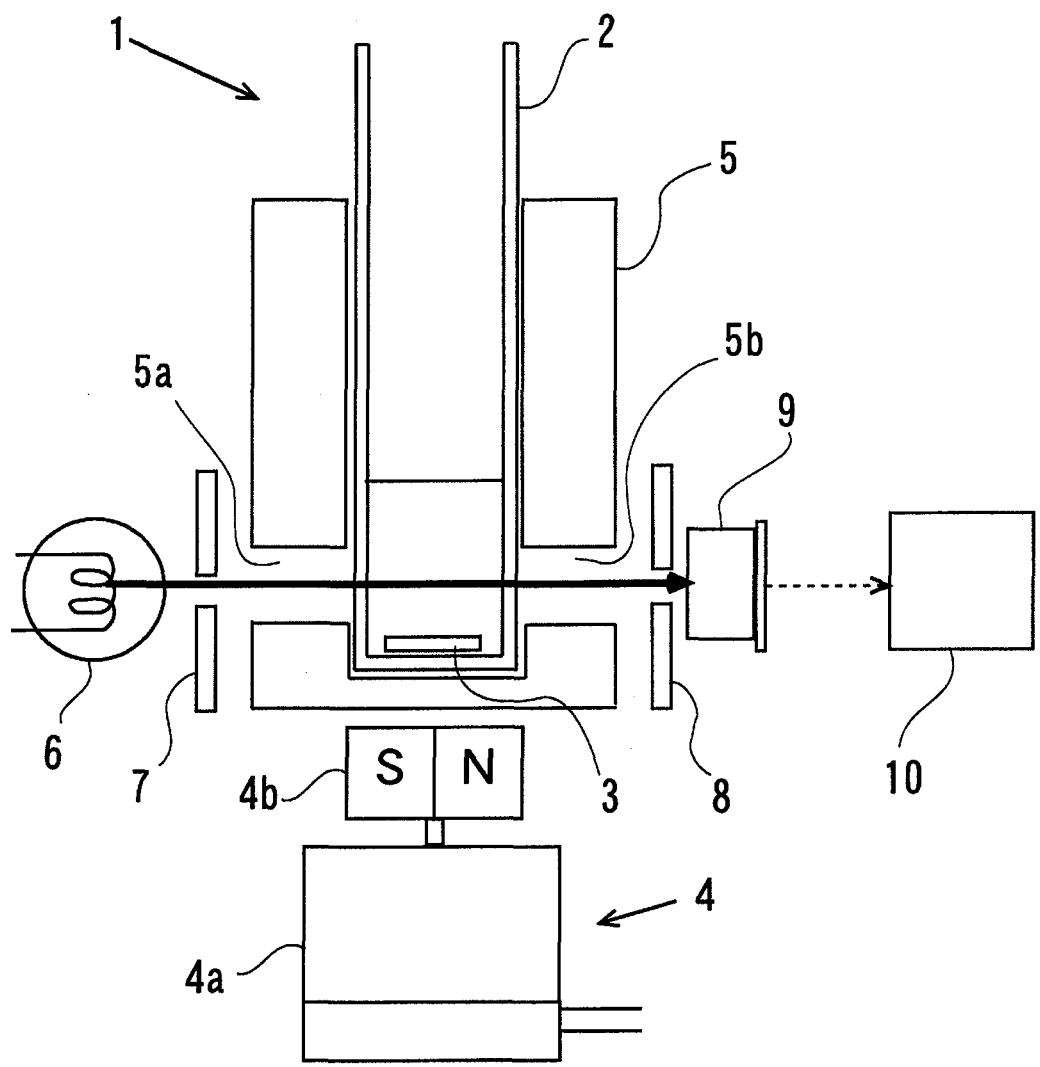
FIG. 1 is a diagram illustrating a schematic configuration of a turbidimetric measurement apparatus according Example 1 of the present invention.

FIG. 1 is a diagram illustrating a schematic configuration of a turbidimetric measurement apparatus 1 as an apparatus for endotoxin measurement of this example. In the turbidimetric measurement apparatus 1 of this example, endotoxin is measured by a stirring turbidimetric method. In this example, an endotoxin-containing sample of a prepared dilution series is poured into a cuvette 2 provided as a liquid mixture retaining means manufactured in Production Example 1. A warmer 5 is mounted so that it surrounds the cuvette 2. An electrically heating wire (not illustrated) is installed in the warmer 5. Thus, the cuvette 2 can be kept at about 37° C. by energizing the electrically heating wire. In the cuvette 2, a stainless-steel stirring bar 3 is placed. The stirring bar 3 rotates in the cuvette 2 by the action of a stirrer 4 placed under the cuvette 2. In other words, the stirrer 4 includes a motor 4a and a permanent magnet 4b mounted on an output shaft of the motor 4a. The motor 4a is energized to rotate the permanent magnet 4b. Since the magnetic field from this permanent magnet 4b rotates, the stainless-steel stirring bar 3 can be rotated by the action of the rotating magnetic field. The stirring bar 3 and the stirrer 4 are equivalent to the stirring means. In this example, the rotational speed of the stirring bar 3 was set to 1000 rpm.

Here, the turbidimetric measurement apparatus 1 is provided with a light source 6 as a light incidence means and a light receiving element 9 as a light receiving means. The light emitted from the light source 6 passes an aperture 7 and then passes through a light incident hole 5a formed in the warmer 5, followed by being incident on the sample in the cuvette 2. The light transmitted through the sample into the cuvette 2 is then output from an emission hole 5b formed in the warmer 5 and then passes through an aperture 8. Subsequently, the light is irradiated on the light receiving element 9. The light receiving element 9 outputs a photoelectric signal in response to the intensity of the received light. The output of the optoelectric signal is incident on an arithmetic unit 10 that serves as a determining means and a deriving means. The arithmetic unit 10 determines a reaction-starting time and derives the concentration of endotoxin according to a previously stored program (algorithm). Here, the turbidimetric measurement apparatus 1 may further include a display unit for displaying the derived endotoxin concentration.

Figure 2:
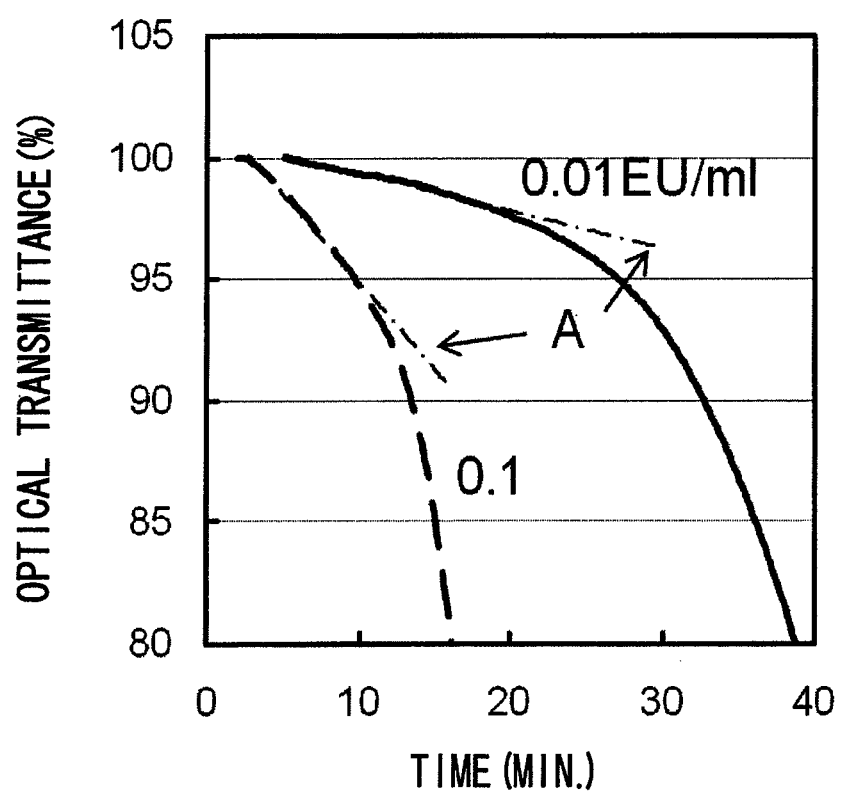
FIG. 2 is a graph illustrating a change over time in optical transmittance, where the graph is provided for describing progressive decrease occurred in Example 1 of the present invention.

A progressive decrease observed in this example is illustrated in FIG. 2. This progressive decrease is a phenomenon notably appearing in portions indicated by "A" in the figure. This is a phenomenon in which the baseline of optical transmittance decreases from immediately after the measurement start regardless of the conditions of a reaction between endotoxin and LAL in a liquid mixture. Then, when the reaction between the endotoxin and LAL proceeds, it is confirmed that a state leads to a change with a further increase in inclination after passing through an inflection point.

In the conventional stirring turbidimetric method, a time at which the optical transmittance becomes lower than 95% has been used as a reaction-starting time. However, when a progressive decrease occurs, the time at which the optical transmittance becomes lower than a threshold of 95% may be abnormally early due to the influence of the lowered baseline. Alternatively, the value of the optical transmittance may become lower than a threshold of 95% before the decreasing curve of optical transmittance reaches an inflection point. Thus, the progressive decrease may lead to a decrease in accuracy of the determination of a reaction-starting time.

Figure 3:
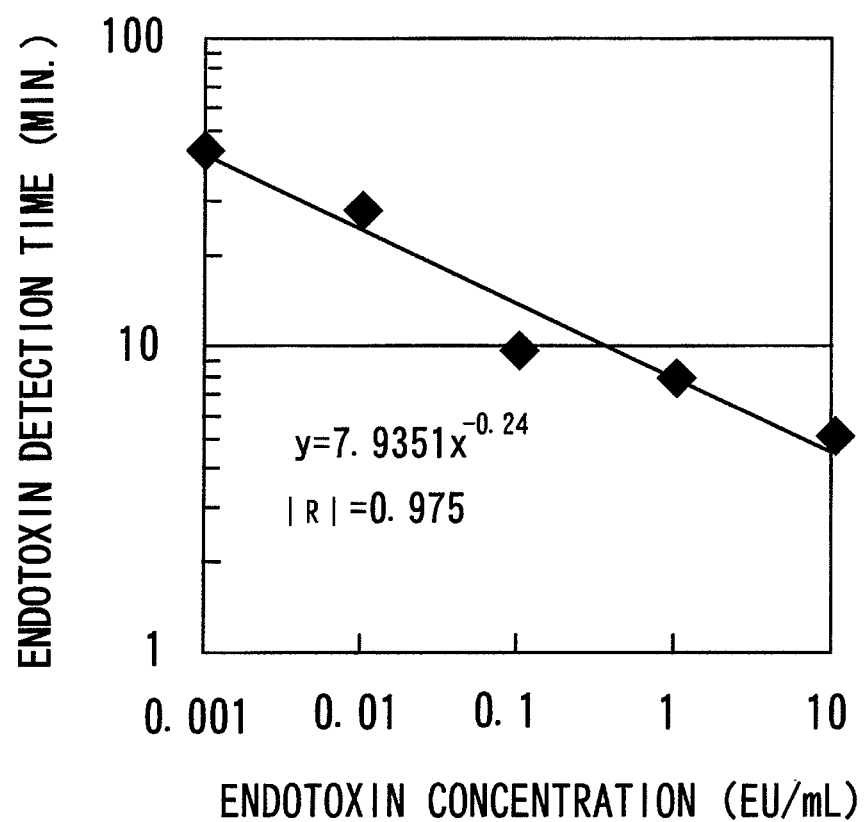
FIG. 3 is a graph illustrating the relationship between the concentration of endotoxin and an endotoxin detection time, where the concentration of endotoxin is obtained by the conventional threshold method.

The conventional threshold method is used and the results are illustrated in FIG. 3, where the concentration of endotoxin is plotted on the horizontal axis and the time at which an endotoxin detection time is lower than a threshold of 95% in the conventional method is plotted on the vertical axis. It has been known that double logarithmic plots in this graph draw a straight line. The absolute value of a correlation coefficient in the results illustrated in FIG. 3 was 0.975. According to the Japanese Pharmacopoeia, the condition "the absolute value of the correlation coefficient shall be greater than or equal to 0.980" is imposed, but the results illustrated in FIG. 3 do not fulfill this condition.

Figure 4:
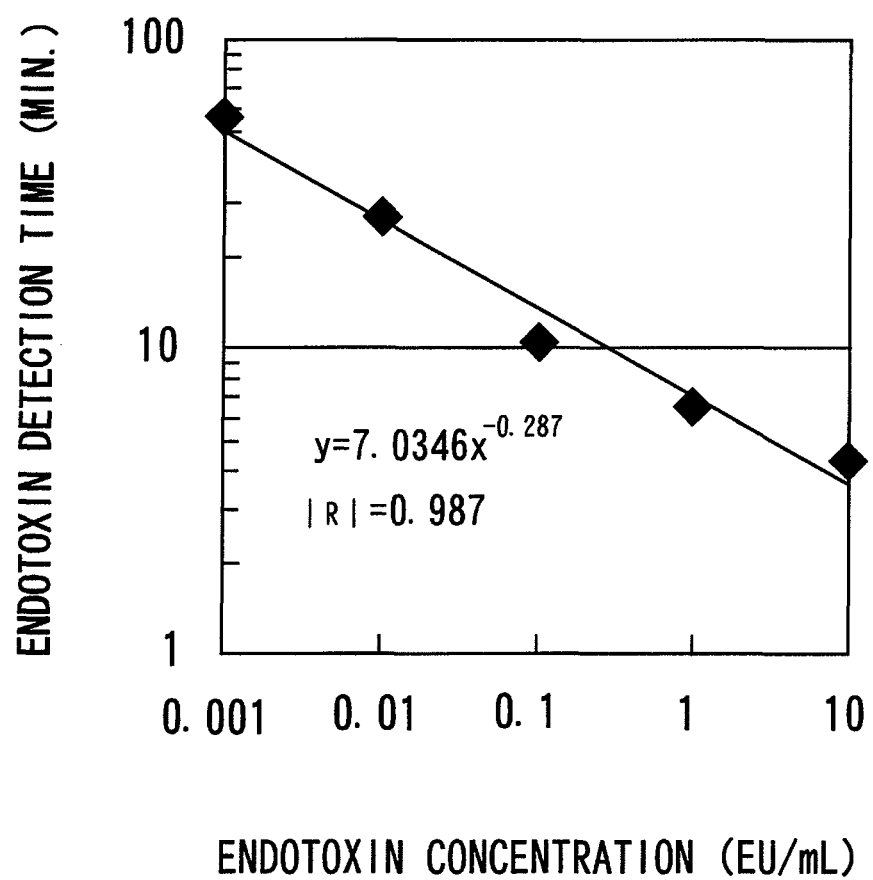
FIG. 4 is a graph illustrating the relationship between the concentration of endotoxin and an endotoxin detection time, where the concentration of endotoxin is determined using a difference method, in accordance with Example 1.

FIG. 4 illustrates the results obtained using the difference method of the present example. In this case, the time interval ΔT was set to 2 minutes and a threshold for determination of a reaction-starting time was set to a time at which the absolute value of a variation in optical transmittance (%) exceeded 1%. As is evident from the figure, the absolute value of the correlation coefficient in the relationship between the endotoxin concentration and the endotoxin detection time was 0.987 when the difference method was applied. In other words, the results representing the stronger correlation were obtained by the application of the difference method, so that the linearity was improved and the conditions in the above Japanese Pharmacopoeia were satisfied. Thus, in this embodiment, the influence of a progressive decrease can be removed only by changing a program (algorithm) in the arithmetic unit 10 of the turbidimetric measurement apparatus 1. Thus, the measurement accuracy of the turbidimetric measurement apparatus 1 can be improved.

Furthermore, in this example, the value of the optical transmittance is equivalent to the detected value and the detected signal value. The turbidimetric measurement apparatus 1 of the present example may be designed so that the time interval ΔT and the threshold will be adjustable in the apparatus 1 itself. Thus, the aforementioned estimating method can be more easily performed.

Example 2

Figure 5:
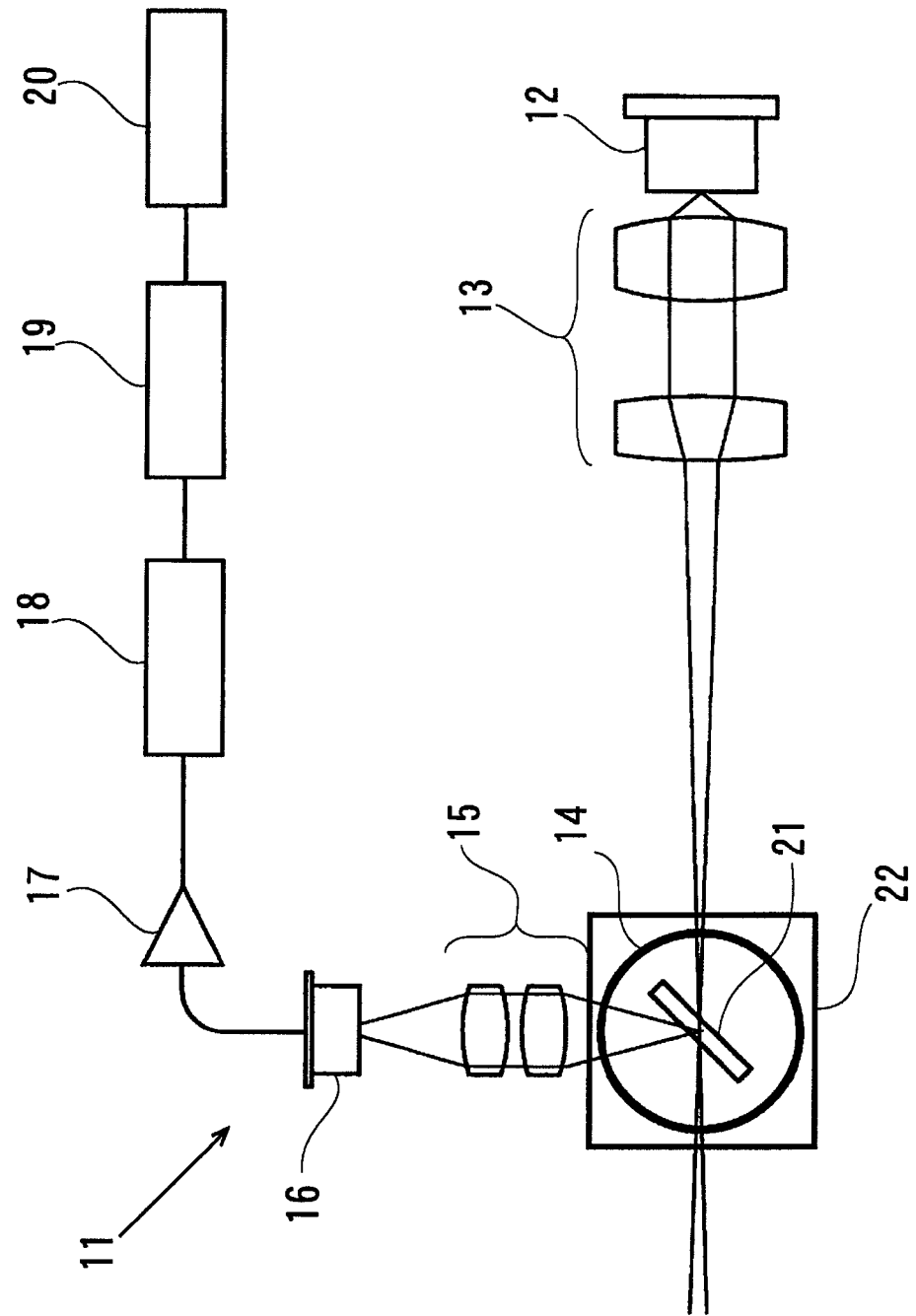
FIG. 5 is a diagram schematically illustrating a configuration of a light scattering particle counting apparatus according to Example 2 of the present invention.

Next, the measurement using the light scattering method will be described as a second example. FIG. 5 is a diagram schematically illustrating a configuration of a light scattering particle counting apparatus 11 as an apparatus for endotoxin measurement according to the present embodiment. A light source 12 used in the light scattering particle counting apparatus 11 is a laser light source. Alternatively, it may be a super-high-intensity LED or the like. Light irradiated from the light source 12 is concentrated by an incidence optical system 13 and then incident on a sample cell 14. The sample cell 14 retains a liquid mixture containing a sample for endotoxin measurement and a LAL reagent. Light incident on the sample cell 14 is scattered by particles (measuring objects, such as coagulogen monomers and coagulogen oligomers) in the liquid mixture.

An output optical system 15 is arranged on the lateral side of an incident optical axis in the sample cell 14. In addition, a light receiving element 16 is arranged on the extension of the optical axis of the output optical system 15. Here, the light receiving element 16 is provided for receiving scattered light, which is scattered by particles in the liquid mixture in the sample cell 14 and concentrated by the output optical system 15, and converting the received light into an electric signal. The light receiving element 16 is electrically connected to an amplifying circuit 17 for amplifying the electric signal photoelectrically converted by the light receiving element 16; a filter 18 for removing a noise from the electric signal amplified by the amplifying circuit 17; an arithmetic unit 19 for calculating the number of gel particles from the number of peaks of the electric signal after the noise removal, determining a reaction-starting time, and deriving the concentration of endotoxin; and a display unit 20 for displaying results.

Furthermore, the sample cell 14 is provided with a stirring bar 21 for stirring a liquid mixture as a sample, where the stirring bar 21 can be rotated by receiving an electromagnetic force from the outside. A stirrer 22 is arranged on the outside of the sample cell 14. Thus, the presence or absence of stirring and the speed of stirring can be regulated.

Here, the sample cell 14 is a cuvette manufactured in Production Example 1, and is equivalent to the liquid mixture retaining means of this example. The light source 12 and the incidence optical system 13 are equivalent to the light incidence means. The stirring bar 21 and the stirrer 22 are equivalent to the stirring means. The output optical system 15 and the light receiving element 16 are equivalent to the light receiving means. The arithmetic unit 19 is equivalent to the determining means and the deriving means.

Figure 6:
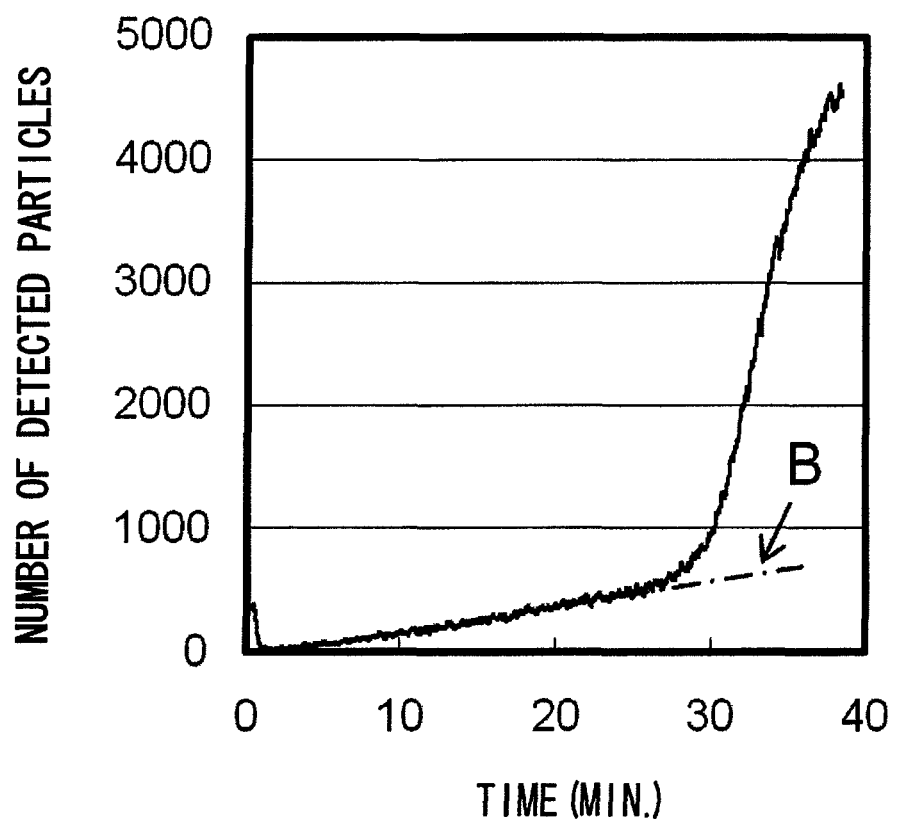
FIG. 6 is a graph illustrating changes in the number of detected particles over time, where the graph is provided for describing progressive increase occurred in Example 2 of the present invention.

FIG. 6 illustrates changes in the number of detected particles over time when the light scattering method is used. In this example, the measurement of endotoxin was performed while being kept at 37° C. under the same sample-stirring condition as that of a stirring turbidimetric apparatus. Specifically, the measurement apparatus used was PA-200 manufactured by Kowa Company Ltd. As is evident from "B" in FIG. 6, a phenomenon, where the light scattering method caused an increase in the number of detected (gel) particles regardless of the state of a reaction between endotoxin and LAL, was confirmed. This reaction caused the threshold (the number of detected particles was 200) to be exceeded before "a rapid increase in the number of particles", which should be detected in the first place. Thus, a correct determination was hardly performed.

Next, a measurement process in this example to which a difference method is applied in contrast to the light scattering method is described. The arithmetic unit 19 generates histogram data with a peak of 1 second every second from an electric signal after the noise removal. Then, the total number of particles detected per second was calculated with reference to the histogram data. In order to smooth variations in the number of particles, the total number of particles calculated per second is moving added for 10 seconds. A moving addition value for 10 seconds obtained by the moving addition is compared with another moving addition value which is obtained at a time corresponding to the time interval $\Delta T$ (=100 seconds) earlier than the former. Then a reaction-starting time is determined as a first histogram data acquisition time after all the differences (increments) continuously obtained 10 times (10 seconds) exceed a threshold of 200.

Figure 7:
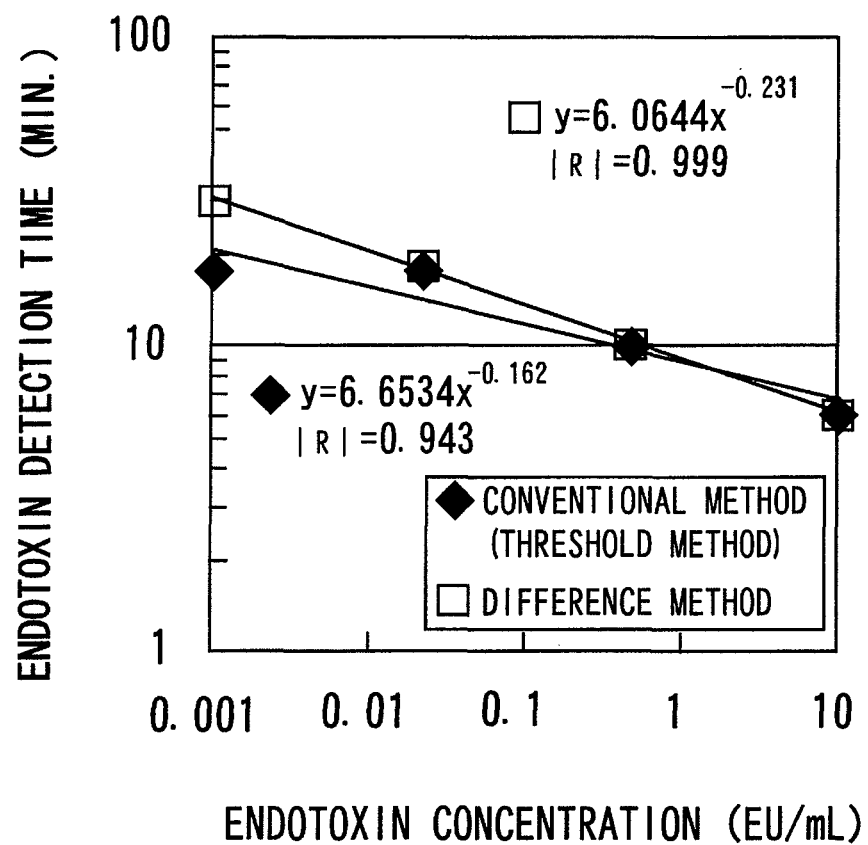
FIG. 7 is a graph illustrating the relationship between the concentration of endotoxin and an endotoxin detection time, where the concentration of endotoxin is obtained by each of the threshold method and the difference method, in accordance with Example 2 of the present invention.

FIG. 7 is a diagram illustrating the results obtained by using the threshold method and the difference method to the light scattering method and plotting the concentration of endotoxin on the horizontal axis and plotting the reaction-starting time on the vertical axis. When the number of particles was simply employed as a detection target, the linearity was severely broken as represented by the absolute value of correlation coefficient, 0.943. In contrast, in the case where a time interval $\Delta T$ was set to 100 seconds and a reaction-starting time was defined at a time when the increment of the number of particles for 100 seconds exceeded 200, a strong correlation was obtained as the absolute value of correlation coefficient was 0.999. From the above description, an algorithm in which a detection target is the increment of the number of particles for 100 seconds can be a stable algorithm compared with the conventional one in which the detection target is the number of particles. Therefore, in the present example, the influence of progressive increase can be removed by only changing a program (algorithm) in the arithmetic unit 19 of the light scattering particle counting apparatus 11. As a result, the measurement accuracy of the light scattering particle counting apparatus 11 can be improved.

In this example, furthermore, the value of the number of detected particles (number of gel particles) is equivalent to the detected value and the detected signal value. Furthermore, the light scattering particle counting apparatus 11 may be designed so that the time interval $\Delta T$ and the threshold will be adjustable in the apparatus 11 itself. Thus, the aforementioned estimating method can be more easily performed.

In this example, as described above, the arithmetic unit 19 calculates the total number of particles detected per second from histogram data. The total number of particles is moving added for 10 seconds. A moving addition value for 10 seconds is compared with another moving addition value which is obtained at a time corresponding to the time interval $\Delta T$ earlier than the former. Then a reaction-starting time is determined as a first data acquisition time after all the differences (increments) continuously obtained 10 times (10 seconds) exceed a threshold. However, this measurement process is illustrative only. The detection time of histogram data, the presence or absence of moving addition or moving addition time, the number of times the difference (increment) exceeds the threshold at the time of determining a reaction-starting time, and so on are not limited to their respective values in the present example and can be changed appropriately.

Example 3

A toxinometer (Wako Pure Chemical Industries, Ltd.), which is a conventional apparatus for turbidimetric method, was used for the measurement of endotoxin. In the toxinometer (turbidimetric method) that does not stir a sample, a progressive decrease in baseline of unknown cause was found in changes in optical transmittance over time. Therefore, the toxinometer, which uses the threshold method where a reaction-starting time is the time of exceeding 95%, generates a measurement result influenced by a progressive decrease. Thus, to improve the measurement accuracy, a reanalysis was performed using the difference method in a manner described above. As a result, the linearity of a regression line increases. The influence of a detection error on the endotoxin measurement was prevented by the difference method. Thus, an improvement was observed.

In each of the above examples, furthermore, the phrase "difference exceeds the threshold" does not always mean that the difference changes from a state of being smaller than the threshold to a state of being larger than the threshold. Naturally, for example, the phrase also means that the difference, which tends to be decreased, changes from a state of being larger than the threshold to a state of being smaller than the threshold.

Furthermore, even when the above difference method is used, the measurement within a realistic time period has been difficult in some cases of using a constant time interval for acquiring absorbance or the number of gel particles. This is because, as described above, a sufficiently large difference value is hardly obtained in the measurement of a predetermined physiologically active substance of a low concentration, where the transition of the change curve of absorbance or the number of gel particles is slow. Hereafter, the case where the countermeasures for this point are incorporated will be described.

In the present invention, the difference method is further modified so that the time interval for acquisition of a difference in absorbance or a difference in the number of gel particles varies with acquisition time. More specifically, the time interval for acquiring a difference in absorbance or a difference in the number of gel particles is defined as a time function from the start of measurement. Then the time interval is designed so that it will be changed over time or a plurality of series with different time intervals is previously prepared. In the following description, unless otherwise noted, the description will be made with reference to an exemplary endotoxin measurement for a reaction of LAL with endotoxin.

The measurement of predetermined physiologically active substance requires reagents and preparation water without contamination of these substances, and laboratory instruments without attachment of these substances. For dissolving a reagent or preparing a dilution series of endotoxin, an injection solvent (manufactured by Otsuka Pharmaceutical Co., Ltd.) with an extremely small contamination amount of endotoxin was used. Furthermore, consumable supplies, such as pipette tips, used were materials individually packed and clearly indicated "endotoxin free". Since measurement vessels used were made of glass materials, the measurement vessels were subjected to a common treatment of inactivating endotoxin (dry-heat treatment).

Production Example 2

Glass Vessel for Measurement

A stainless-steel stirring bar for stirring (4.5 mm, 0.7 mm in thickness) was placed in a measurement glass vessel (6 mm in diameter) and the opening of the vessel was covered with aluminum foil. Twenty glass vessels, which were bundled together and covered with aluminum foil, were provided as one package. Then a plurality of the packages was collected and placed in a dry-heat sterilization metal can. Subsequently, the can was closed with a lid and then subjected to a dry-heat treatment at 250° C. for 3 hours.

Hereinafter, an example will be described. In this example, the difference method is further modified so that the time interval for acquisition of a difference in absorbance or a difference in the number of gel particles varies with acquisition time. In the following example, absorbance was employed as a physical quantity that varies with a reaction of LAL with a predetermined physiologically active substance. However, the present invention is not limited to measurement target substances, measurement reagents, and the physical quantities of the measurement target substances shown in the following examples. In the following description, a technique for acquiring difference values at time intervals defined by a time function, which has been described above, is referred to as a "time-function difference method". A technique for acquiring a difference value using a plurality of series having different time intervals is referred to as a "multi-series difference method".

The turbidimetric measurement apparatus used for acquiring absorbance in the present example is equivalent to one illustrated in FIG. 1.

Comparative Example

Usual Difference Method with Constant Time Interval

In this embodiment, first, the measurement of endotoxin was performed using a usual difference method with constant time intervals as a comparative method to verify the effects of the time-function difference method and the multi-series difference method. A Limulus reagent used was "Limulus ES-II Single Test" (manufactured by Wako Pure Chemical Industries, Ltd.). A dilution series of endotoxin concentrations of 1.0, 0.1, 0.01, and 0.001 EU/mL was prepared and each reacted with the Limulus reagent in the cuvette 2. Absorbance was recorded and analyzed using the turbidimetric measurement apparatus 1 (absorbance measurement apparatus (EX-100: Kowa Company Ltd).

Figure 8:
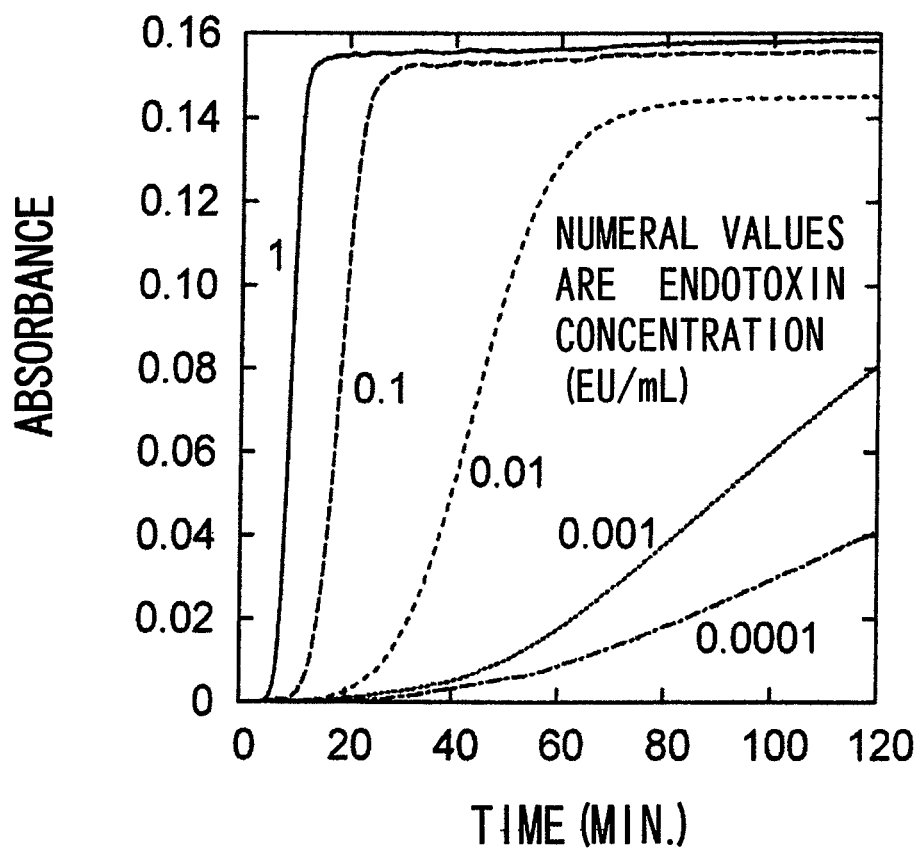
FIG. 8 is a graph illustrating that a change in absorbance over time obtained by a usual difference method varies depending on the concentration of endotoxin.

To acquire difference values, a process for setting a time interval constant was used as described above. The time interval was set to 3 minutes. Difference values were recorded over time, while a reaction-starting time (detection time) was set to a time at which the difference value of absorbance exceeded a threshold. The threshold used was 0.003. Absorbance change curves of the respective samples are illustrated in FIG. 8 and change curves of absorbance difference values over time are illustrated in FIG. 9.

Figure 9:
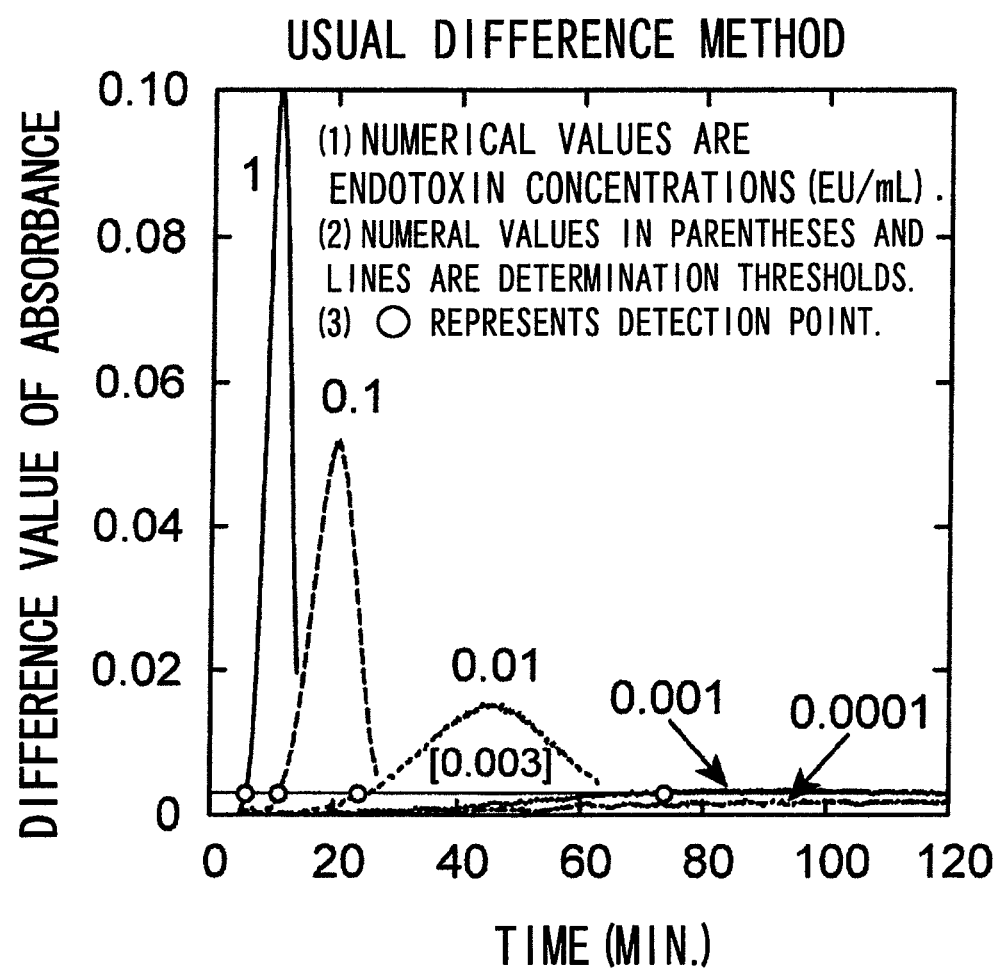
FIG. 9 is a graph illustrating that a change in difference value of absorbance over time obtained by a usual difference method varies depending on the concentration of endotoxin.

As is evident from FIG. 9, the usual difference method with a constant time interval for the times of acquisition of absorbance difference values was able to measure endotoxin within an endotoxin concentration range of 1.0 to 0.001 EU/mL. However, when the concentration of endotoxin 0.0001 EU/mL, which is below the above range, the detection was failed because any absorbance difference value was not so high as to exceed the threshold.

Example 4

Time Function Difference Method

Next, a time function difference method where a time interval for acquisition of a time difference is defined by a time function will be described as Example 4. Here, when low-concentration endotoxin was reacted with LAL, the absorbance varies slowly. Thus, there is a need of using a function that extends a time interval over time. Specifically, the time interval may be changed linearly with time from the start of measurement (linear function) or it may be changed by definition with a polynomial of one variable, such as a quadratic function or a cubic function. Alternatively, an exponential function, a logarithmic function, or the like may be used. In fact, for example, the absorbance data obtained from the turbidimetric measurement apparatus 1 is sampled with a fixed time interval, such as a one-second interval, in many cases. In this event, therefore, the above exemplified function and the apparatus-specified fixed time interval may be combined and the resulting discontinuous time interval function may be employed.

Here, a change in difference value of absorbance was obtained by the time-function difference method using the data of each absorbance change curve obtained in the above comparative example. The turbidimetric measurement apparatus 1 used for the measurement is designed to output data at intervals of 1 second. Thus, the time function cannot be defined by a continuous function. Here, the time interval I (min.) for calculating a difference value was defined as a discontinuous function as represented by equation (1).

$$I = \text{floor}(T/10) + 1 \tag{1}$$

However, T is the time (min.) from the start of measurement.

The function "floor (X)" represents a floor function. Here, the threshold was set to a constant value of 0.01. Under the present conditions, a change in difference value of absorbance was obtained by the time function difference method.

Figure 10:
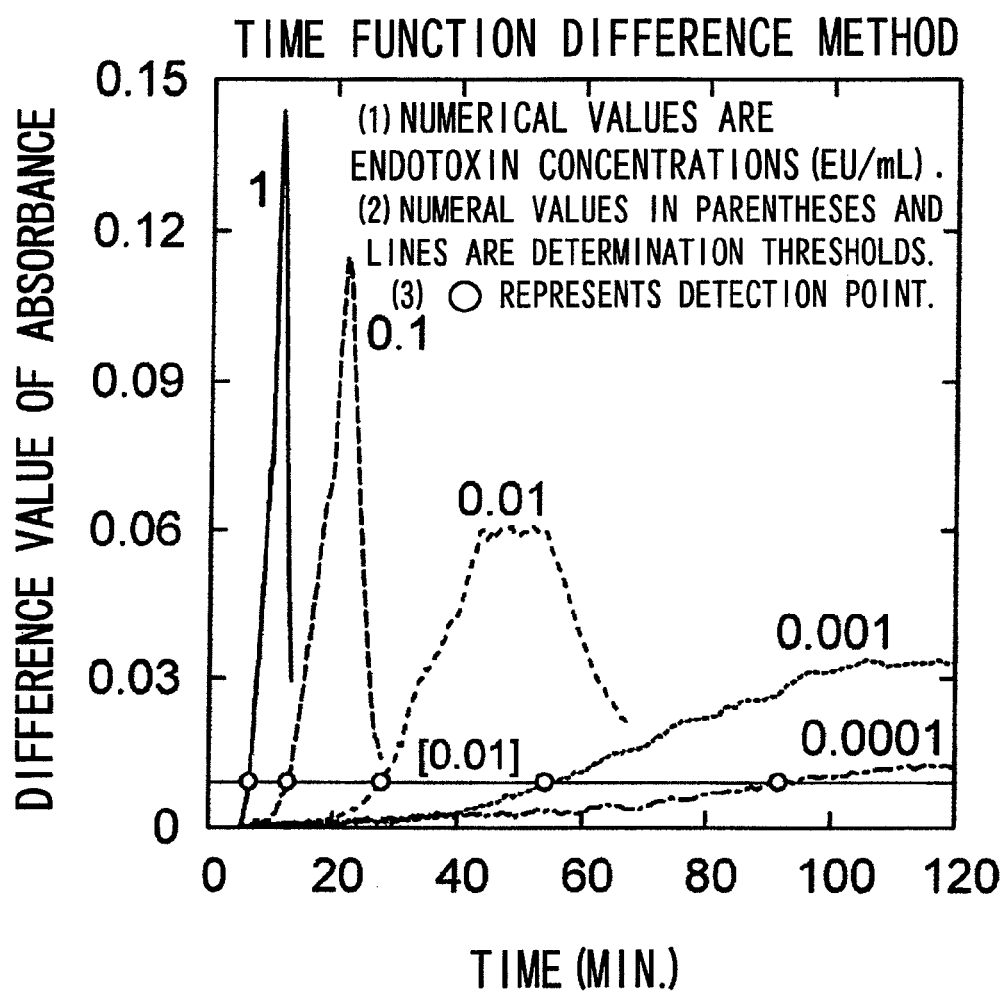
FIG. 10 is a graph illustrating that a change in difference value of absorbance overtime obtained by a time function difference method varies depending on the concentration of endotoxin in accordance with Example 4 of the present invention.

The results thus obtained are represented in FIG. 10 as a time-dependent change curve of an absorbance difference value with respect to each sample of a dilution series. As is evident from FIG. 10, the curves of absorbance difference values at low endotoxin concentrations, such as 0.001 EU/mL and 0.0001 EU/mL, represent larger values compared with those of the comparative example illustrated in FIG. 9. In both cases, it is possible to determine a reaction-starting time at a realistic measurement time.

In this example, during an early stage of the measurement in which a progressive decrease/increase does not appear in the reaction between LAL and endotoxin, the difference value of absorbance is almost constant. Thus, the initial difference value may be recorded and it may be subtracted as a background value from a difference value at each time. In this case, it is possible to reduce any influence on the measurement of progressive decrease/increase.

However, in the present example, the time interval is changed with the time function. Thus, the time interval for obtaining a difference is increased even if there is a linear change in progressive decrease/increase. As a result, the difference value due to the progressive decrease/increase is also increased as a time function. Therefore, the influence of progressive decrease/increase on the measurement cannot be completely removed. To deal with this case, the following measure may be taken. For example, the difference value at the early stage of the reaction is stored as a background value. Then, the background value is multiplied by a factor which is obtained as a ratio between the time interval at each acquisition time and the initial time interval. The resulting value is subtracted from a difference value obtained at each acquisition time.

Furthermore, the threshold of the difference value in the present example may be a constant value regardless of a time from the start of measurement as described above or may be a threshold to be varied with a time function. In fact, a low concentration of a predetermined physiologically active substance causes a very slow change in absorbance when the predetermined physiologically active substance is reacted with LAL. Thus, in the case of using a time function, the absolute value of the threshold may be defined so that it will be decreased with time. In this case, the envisaged time function to be used may be a linear function, polynomial of one variable, or the like.

Alternatively, when a graph of a time-dependent change in absorbance difference value for each endotoxin concentration as shown in FIG. 9 is obtained in advance, a threshold may be defined using a curve obtained by connecting the values for example 20% of the peaks of the curves for the respective endotoxin concentrations. Then, even when the endotoxin concentration is low, a difference value that exceeds the threshold can be obtained more reliably. Furthermore, the threshold may be defined using a curve which is in inverse proportion to elapsed time from the measurement start.

Figure 11:
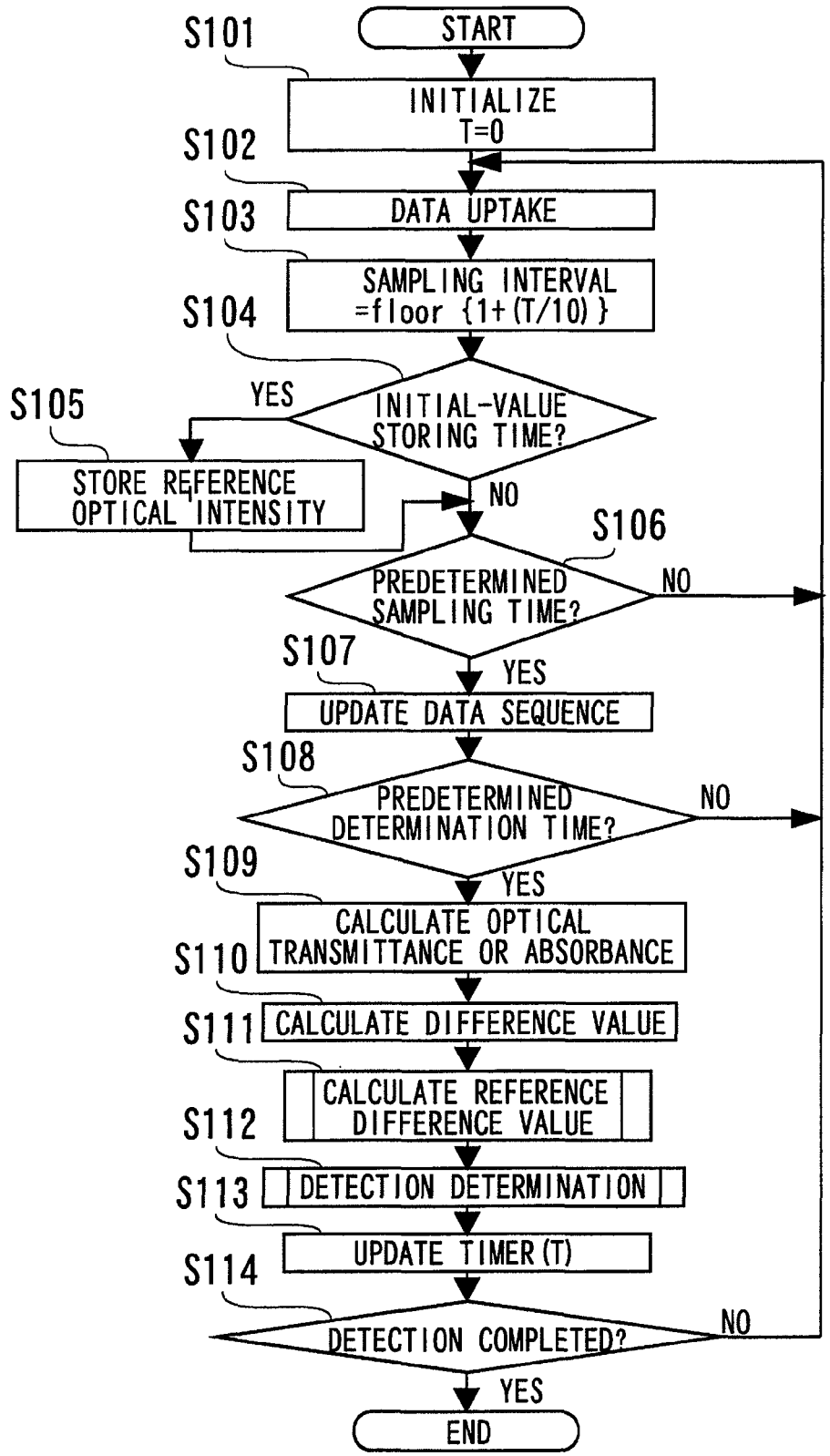
FIG. 11 is a flowchart illustrating a measurement routine for endotoxin measurement by the time function difference method in accordance with Example 4 of the present invention.

FIG. 11 is a flowchart illustrating a measurement routine for endotoxin measurement by the above-described time function difference method. This routine is a program executed by the arithmetic unit 10 with the start of measurement. First, an initializing operation is performed in S101 when the routine is executed. The value of variable T, a time from the start of measurement, is reset. Then, the process proceeds to S102, and data of a photoelectric signal according to the intensity of light received by the light receiving element 9 is incorporated into the arithmetic unit 10. Subsequently, the process proceeds to S103, and a time interval I (min.) for calculating a difference value is calculated based on the value of T at present according to the equation (1).

Next, in S104, it is determined whether this time is a time of storing the initial value of absorbance. In the present example, the time of storing the initial value of absorbance is set to 1 second from the start of measurement. When an affirmative decision is made in S104, the process proceeds to S105. When a negative decision is made in S104, on the other hand, the process proceeds to S106. In S105, the initial value (reference optical intensity) of the data of a photoelectric signal according to the intensity of light received by the light receiving element 9 is stored. In S106, it is determined whether the present time is a previously determined sampling time or not. The determination of the sampling time is performed depending on whether the sampling interval calculated in S103 is elapsed with reference to the previous sampling time. When the affirmative decision is made here, the process proceeds to S107. On the other hand, when a negative decision is made here, the process returns to before the processing of S102.

When an affirmative determination is made in S106 (i.e., when the present time is a sampling time), S107 updates a data sequence in a memory installed in the arithmetic unit 10. In other words, the data incorporated in S102 is stored as the newest data in the memory. Subsequently, in S108, it is determined whether the present time is a previously determined determination time. Here, the term "previously determined determination time" means a time for determining whether it is a reaction-starting time or not by comparing the value of difference between the newest data and the previous data with a previously determined threshold. The previously determined determination time may be set simultaneously with the sampling time or these times may be set completely independent from each other. When a negative decision is made in S108, the process returns to before the processing in S102. On the other hand, when the affirmative decision is made in S108, the process proceeds to S109.

In S109, an optical transmittance or absorbance is calculated. The optical transmittance may be calculated by dividing the newest data among the data sequences, by the data previously obtained in the sample-free state. In addition, the absorbance may be calculated by subtracting the calculated optical transmittance from 1. Next, in step S110, a difference value is calculated. In the present example, the calculation may be performed by subtracting the value of optical transmittance or absorbance calculated from data for the last sampling time in the data sequence from the value of optical transmittance or absorbance calculated from the newest data.

In S111, a reference difference value is calculated. In the present example, the reference difference value is calculated by subtracting an optical transmittance or absorbance, which is calculated from data sampled at the first sampling time, from an optical transmittance or absorbance, which is calculated from data sampled at the second sampling time from the start of measurement. This reference difference value is a background value for excluding the influence of the progressive decrease/increase in the present measurement.

Detection determination is performed in S112. Basically, it is determined whether the value obtained by subtracting the reference difference value calculated in S111 from the difference value calculated in S110 is larger than the previously defined threshold. When it is determined continuously five times that it is larger than the threshold, it is determined that a reaction-starting time is detected. When it is lower than the threshold, it is determined that the reaction-starting time is not yet detected. Then, when it is determined that the reaction-starting time is detected, the memory of the arithmetic unit 10 stores the value of the reaction-starting time and the fact that the detection is completed. The details of this processing will be described later.

The value of the timer T is updated in S113. In S114, it is determined whether a reaction-starting time is already detected or not. When it is determined in S112 that the reaction-starting time is detected and stored as one already detected, the present routine is once ended. On the other hand, when it is determined in S114 that the reaction-starting time is not detected, the process returns to before the processing in S102.

Figure 12:
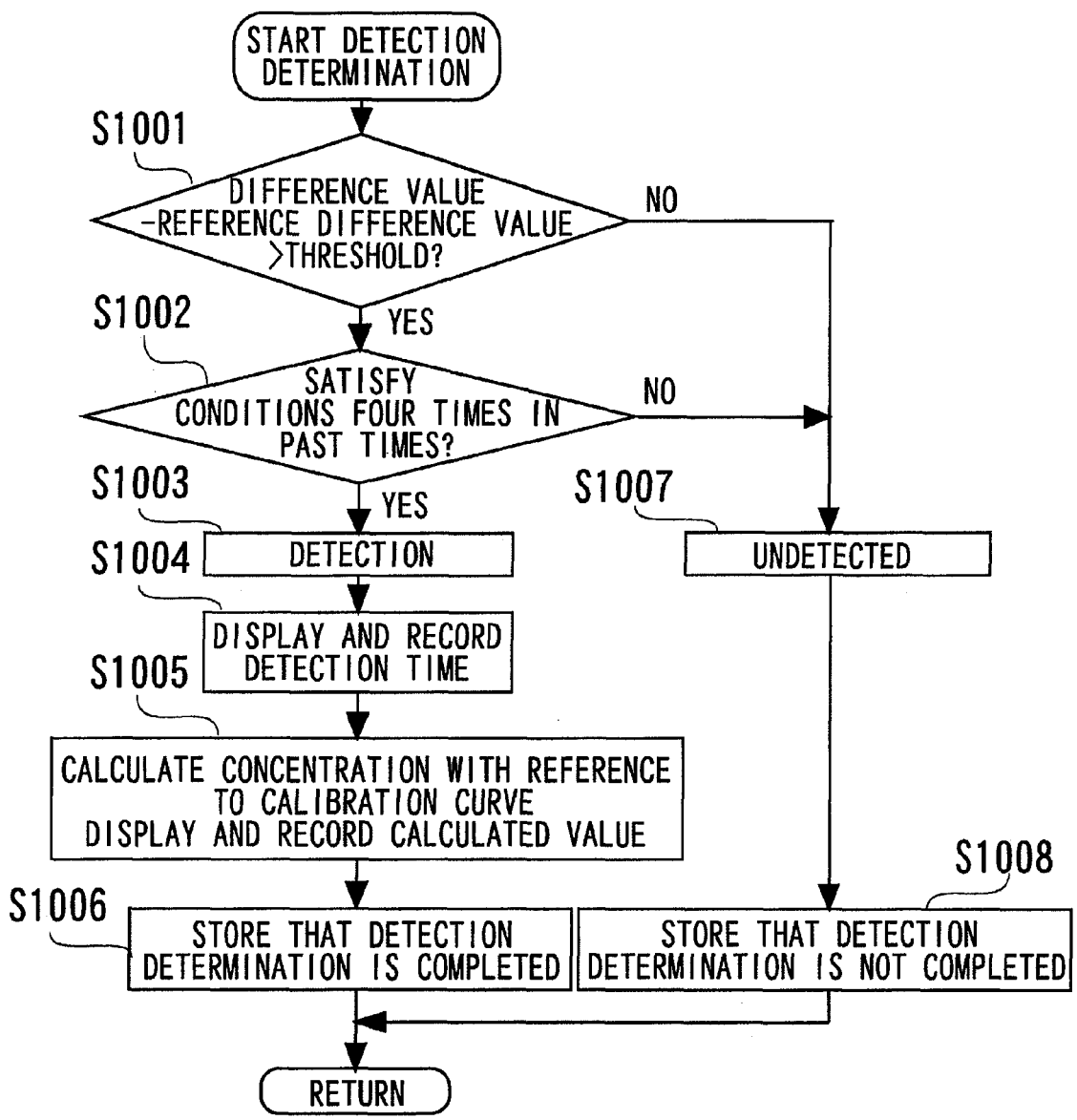
FIG. 12 is a flowchart illustrating a subroutine for detection determination in the measurement routine in accordance with Example 4 of the present invention.

Next, FIG. 12 is a flowchart illustrating a subroutine for detection determination in S112 in the above measurement routine. In S1001, when the present subroutine is executed, it is determined whether a value obtained by subtracting the reference difference value calculated in S111 from the difference value calculated in S110 is larger than a previously defined threshold or not. Here, when an affirmative decision is made, the process proceeds to S1002. On the other hand, when a negative decision is made, then the process proceeds to S1007.

In S1002, it is determined whether the condition of S1001 is satisfied even after the last four determinations or not. Here, when an affirmative decision is made, the process proceeds to S1003. On the other hand, when a negative decision is made, the process proceeds to S1007. In other words, in S1002, it is determined whether a state where the value obtained by subtracting the reference difference value calculated in S111 from the difference value calculated in S110 is larger than the previously defined threshold is satisfied continuously five times.

Next, in S1003, it is determined that the reaction-starting time is detected. On the other hand, in S1007, it is determined that the reaction-starting time is not yet detected. In S1004, the time T at which the reaction-starting time is determined to be detected in S1003 is defined as a detection time (reaction-starting time). Then, the detection time is displayed and stored in the memory of the arithmetic unit 10.

In S1005, the endotoxin concentration is calculated from a map obtained in advance (equivalent to a calibration curve) where the relationship between the endotoxin concentration and the reaction-starting time is stored. Then the value is displayed and stored in the memory of the arithmetic unit 10. In S1006, the fact that the detection determination is completed is stored in the memory of the arithmetic unit 10. On the other hand, in S1008, the fact that the detection determination is not yet completed is stored in the memory of the arithmetic unit 10. When the processing in S1006 or S1008 is ended, the present routine is completed and the process proceeds to S113 of the measurement routine.

Here, the flowchart of the measurement routine illustrated in FIG. 11 and the flowchart of the subroutine illustrated in FIG. 12 are exemplary routines for performing the measurement of the present example. Thus, it is contemplated that the measurement routine is not limited to the flow represented in any of these flowcharts. Furthermore, in S1002 of FIG. 12, it is determined whether a state where the value obtained by subtracting the reference difference value calculated in S111 from the difference value calculated in S110 is larger than the previously defined threshold is satisfied continuously five times. However, this processing is provided for increasing the accuracy of the measurement. Thus, it goes without saying that the number of times of satisfying the above state may be other than five, for example, one.

Example 5

Multi-Series Difference Method

Next, a case where a plurality of series with different time intervals is prepared in advance will be considered as Example 5 of the present embodiment. This case requires two or more series. There is no upper limit of the number of series. More series may be prepared to cope with a measurement that takes a longer times. In this case, a higher-accuracy measurement can be performed. The number of the series which can be prepared is actually restricted by the size and throughput of a storage area of a computer to be used for analysis. If there are many measurable channels of the apparatuses, it is necessary to prepare the corresponding number of series. Therefore, the number of series is preferably 30 or less, more preferably 10 or less per channel.

The time interval assigned to each series is arbitrary. Actually, the time intervals assigned are even intervals of, for example 5, 10, 15, and 20 seconds (linear function). Alternatively, the intervals assigned are exponentially increased, for example, 1, 3, 10, and 30 seconds. Among the difference values obtained at such time intervals, the difference value at the early stage of the measurement start is expected to be zero when a change in absorbance does not include the above progressive decrease/increase. Furthermore, even when a change in absorbance includes progressive decrease/increase, the sampling interval in each series is not changed. Thus, in each series, the initial difference value may be recorded and it may be subtracted as a background value from a difference value at each time. In this case, in each series, the influence of progressive decrease/increase on the measurement can be completely removed.

In the present example, the absorbance difference value was calculated by the multi-series difference method using each absorbance change curve data obtained in the comparative example. The number of series used for acquisition of a difference value is set to three (series name: S1, S2, and S3). Each series has a sequence that can retain the absorbance of 60 data. The sampling intervals of data of each series were determined based on First In First Out (FIFO: a procedure of throwing away the oldest data in the sequence and adding one new data). In other words, the calculation of absorbance and data update work (deletion of the oldest data and the recording of the latest data in the sequence) are carried out every 1 second in S1, 6 seconds in S2, and 30 seconds in S3.

As represented by the following equation (2), the difference value ΔABS of absorbance was calculated by obtaining a difference between values on the opposite ends of a sequence for every series, $$\Delta ABS = A[60] - A[1] \quad (2)$$

In the equation, A[60] represents 60th (latest) absorbance data in a sequence in each series and A[1] represents first (oldest) absorbance data in a sequence in each series. According to the equation (2), the difference values of absorbance for all the series of S1 to S3 were calculated. Here, the initial values P1, P2, and P3 of absorbance, which were obtained at first in the respective series, were acquired. Acquisition timing is 1 minute for P1, 6 minutes for P2, and 30 minutes for P3 from the start.

Figure 13:
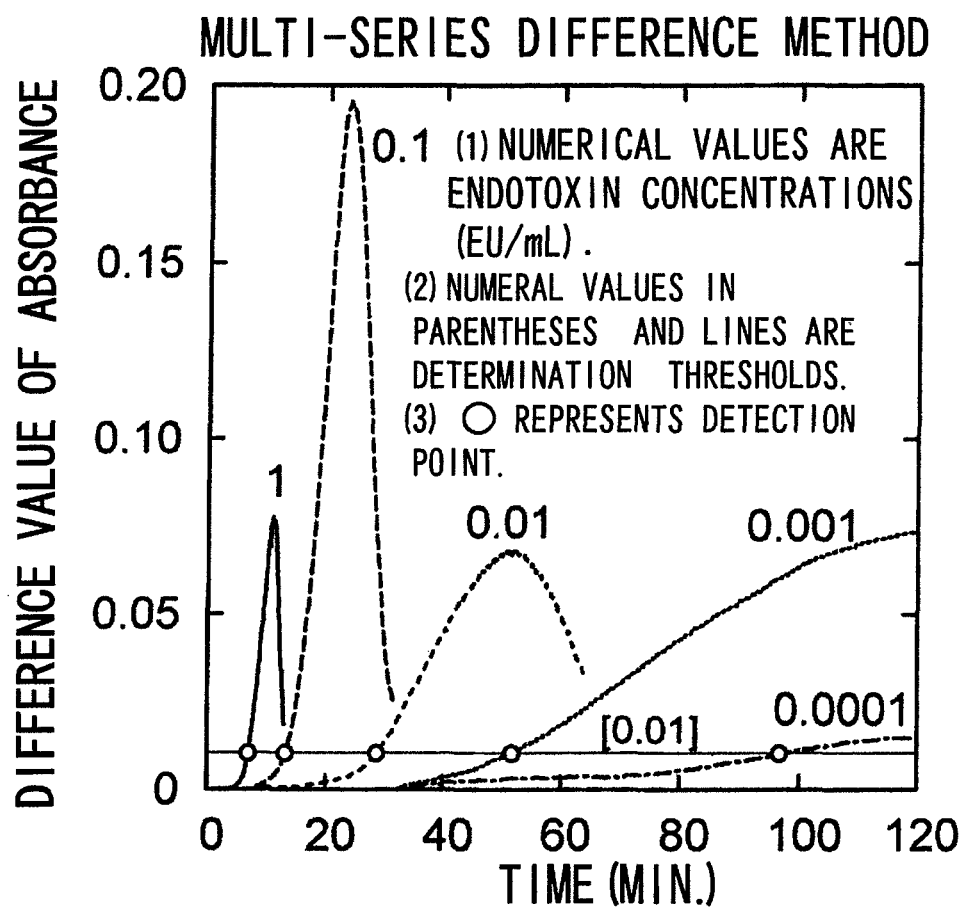
FIG. 13 is a graph illustrating that changes in difference value of absorbance over time acquired by a multi-series difference method varies depending on the concentration of endotoxin, in accordance with Example 5.

The absorbance difference values acquired under the above conditions include progressive decrease/increase to a certain degree. Thus, a value obtained by subtracting the initial value of absorbance from the difference value of absorbance at each time in each series was recorded over time and a reaction-starting time (detection time) was determined as a time at which the difference value of absorbance in any of the series exceeds a threshold. A time-dependent change curve of the absorbance difference value of each sample is illustrated in FIG. 13. As is evident from FIG. 13, the curves of absorbance difference values at low endotoxin concentrations, such as 0.001 EU/mL and 0.0001 EU/mL, represent larger values compared with those of the comparative example illustrated in FIG. 9. In both cases, it is possible to determine a reaction-starting time at a realistic measurement time.

Furthermore, the threshold of the difference value in the present example may be a constant value regardless of a time from the start of measurement as described above or may be a threshold to be varied with a time function. In fact, a low concentration of a predetermined physiologically active substance causes a very slow change in absorbance when the predetermined physiologically active substance is reacted with LAL. Thus, in the case of using a time function, the absolute value of the threshold may be defined so that it will be decreased with time. In this case, the envisaged time function to be used may be a linear function, polynomial of one variable, or the like.

Furthermore, when a plurality of series with different time intervals is prepared in advance, every series shows a different time at which the difference exceeds the threshold. In this case, a method for determining a reaction-starting time employs a time of a first exceeding series. Alternatively, various determination methods, such as one employing an average of two first exceeding series, may be considered. However, the threshold may be exceeded in only one series depending on the concentration of a predetermined physiologically active substance. In order to detect reliably, it is desirable to use a value of a series where the threshold is first exceeded as a reaction-starting time.

Furthermore, in the present example, different thresholds may be used for the respective series. For example, the threshold may be defined as 0.01 for the series S1, 0.005 for S2, and 0.003 for S3. Thus, in the case of measuring a sample with a low concentration of endotoxin, a difference value can exceed a threshold more reliably.

Figure 14:
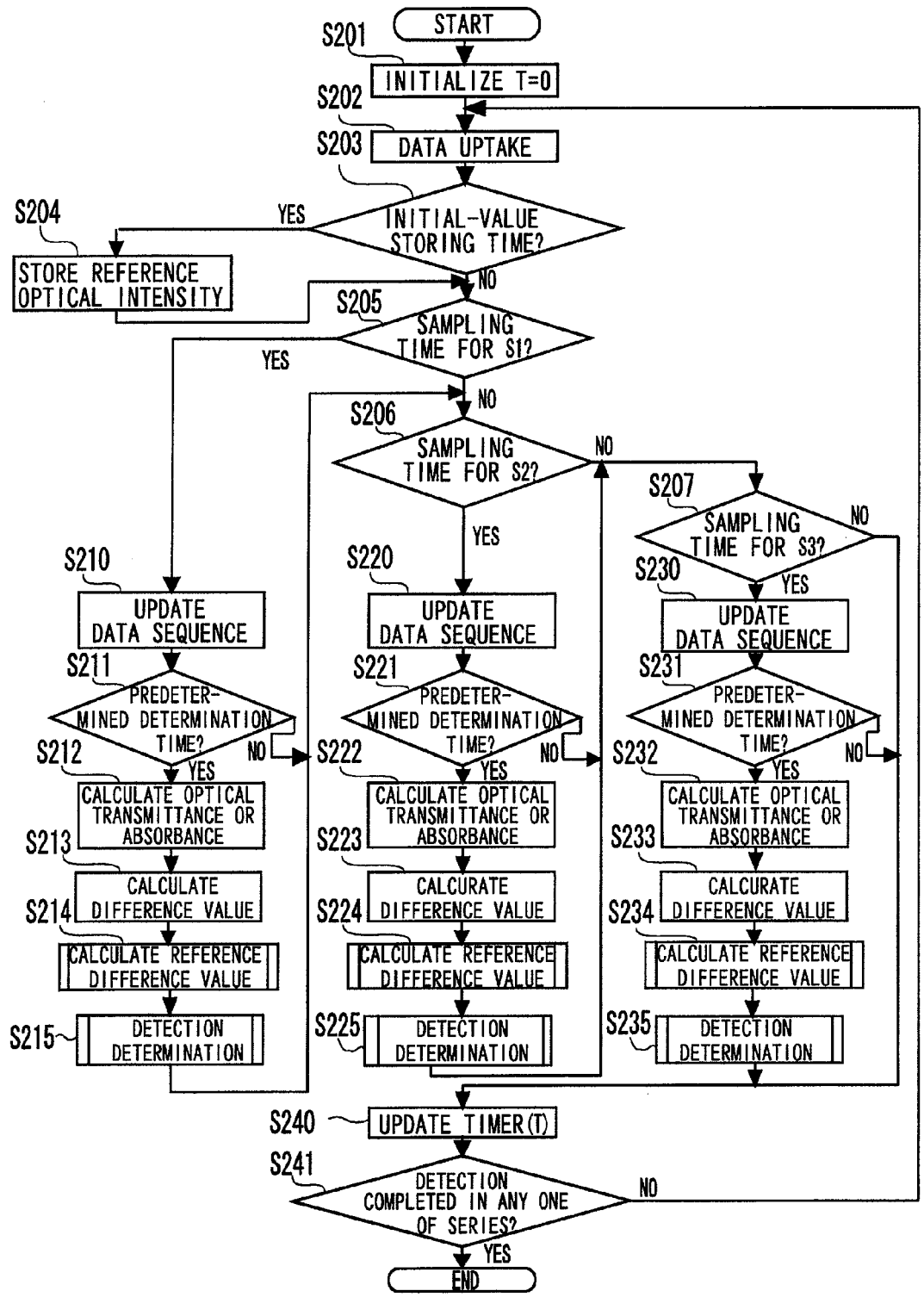
FIG. 14 is a flowchart illustrating a measurement routine 2 in an endotoxin measurement with the multi-series difference method in accordance with Example 5 of the present invention.

FIG. 14 is a flowchart illustrating a measurement routine 2 for endotoxin measurement by the multi-series difference method. This routine is a program executed by the arithmetic unit 10 with the start of measurement. First, an initializing operation is performed in S201 when the routine is executed. The value of variable T, which is a time from the start of measurement, is reset. Then, the process proceeds to S202, and data of a photoelectric signal according to the intensity of light received by the light receiving element 9 is incorporated into the arithmetic unit 10.

Next, in S203, it is determined whether the present time is a time for storing an initial value in any of the series S1, S2, and S3. Here, when the series is S1, the initial-value storing time is set to 1 second after the start of measurement. Here, when the series is S2, the initial-value storing time is set to 6 seconds after the start of measurement. Here, when the series is S3, the initial-value storing time is set to 30 seconds after the start of measurement. When an affirmative decision is made in S203, the process proceeds to S204. On the other hand, when a negative decision is made in S203, the process proceeds to S205.

In S204, the initial value (reference optical intensity) of the light intensity in each series is stored. More specifically, when the present time is determined as an initial-value storing time in the series S1 in S203, the reference optical intensity with respect to the series S1 is stored in S204. When the present time is determined as an initial-value storing time in the series S2 in S203, the reference optical intensity with respect to the series S2 is stored in S204. When the present time is determined as an initial-value storing time in the series S3 in S203, the reference optical intensity with respect to the series S3 is stored in S204.

In S205, it is determined whether the present time is the sampling time for S1. The determination of the sampling time is performed depending on whether the sampling interval (1 sec.) previously set for S1 is elapsed with reference to the previous sampling time for S1. When the affirmation decision is made here, the process proceeds to S210. On the other hand, when a negative decision is made, the process proceeds to S206.

In S206, it is determined whether the present time is the sampling time for S2. The determination of the sampling time is performed depending on whether the sampling interval (6 sec.) previously set for S2 is elapsed with reference to the previous sampling time for S2. When the affirmation decision is made here, the process proceeds to S220. On the other hand, when a negative decision is made, the process proceeds to S207.

In S207, it is determined whether the present time is the sampling time for S3. The determination of the sampling time is performed depending on whether the sampling interval (30 sec.) previously set for S3 is elapsed with reference to the previous sampling time for S3. When the affirmation decision is made here, the process proceeds to S230. On the other hand, when a negative decision is made, the process proceeds to S240.

Processing of S210 to S215 which is executed when the present time is the sampling time for the series S1, processing of S220 to S225 which is executed when the present time is the sampling time for the series S2, and processing of S230 to S235 which is executed when the present time is the sampling time for the series S3 are equal to the processing of S107 to S112 of the measurement routine illustrated in FIG. 11. Therefore, the details of the processing will be omitted herein. Here, in the present routine, when a negative decision is made in S211 and the processing is completed in S215, the process proceeds to before the processing in S206. In addition, when a negative decision is made in S221 and the processing is completed in S225, the process proceeds to before the processing in S207. Furthermore, when a negative decision is made in S231 and the processing is completed in S235, the process proceeds to the processing in S240. Then, the value of timer T is updated.

In S241, it is determined whether the detection is already completed in any series among the series S1 to S3. When an affirmative decision is made, this routine is once ended. On the other hand, when a negative decision is made here, the process returns to before the processing of S202.

Here, the flowchart of the measurement routine 2 illustrated in FIG. 14 is an exemplary routine for performing the measurement of the present example. Thus, it is contemplated that the measurement routine is not limited to the flow represented in any of these flowcharts.

Example 6

Comparison of Each Difference Method

Figure 15:
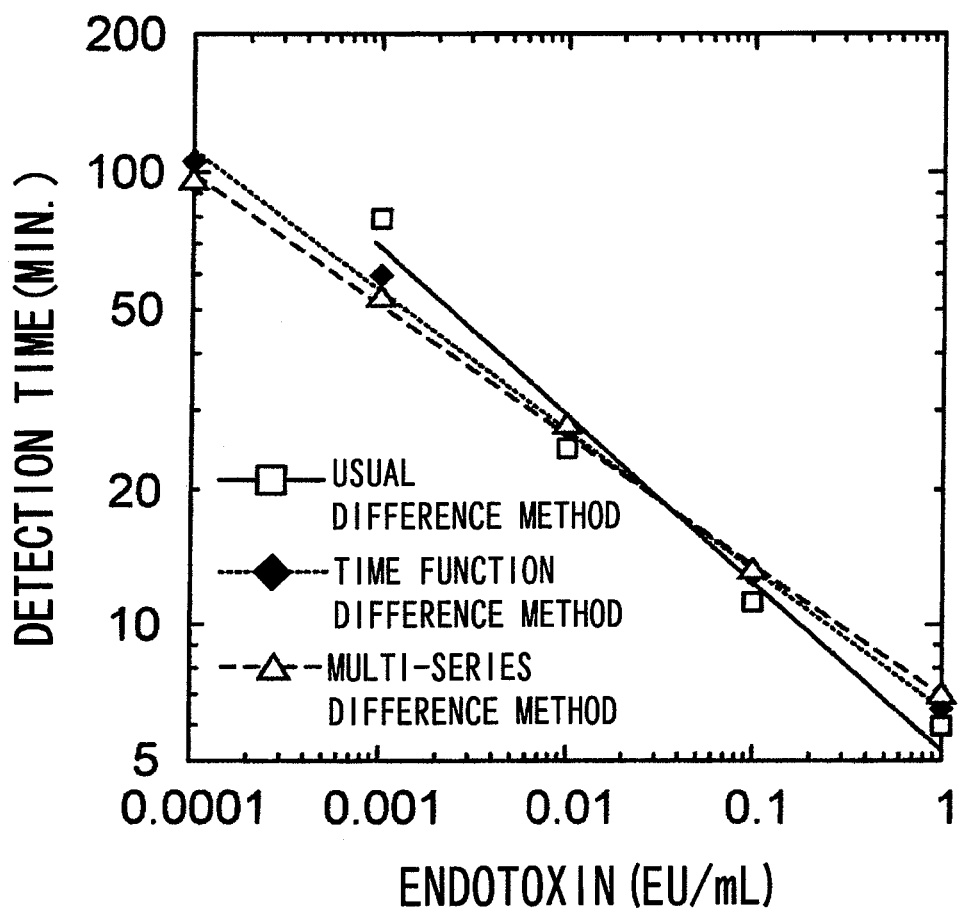
FIG. 15 is a graph illustrating a comparison among the linearity of calibration curves of endotoxin measurement by a stirring turbidimetric method, indifferent difference methods.

The same measurement data was analyzed using techniques described in the comparative example, and Examples 4 and 5. Then, a reaction-starting time was obtained for an aqueous solution sample of an endotoxin dilution series. Then, the reaction-starting times obtained by these methods were compared with one another and the validity of the technique of the present embodiment was evaluated. The relationship between the endotoxin concentration and the reaction-starting time has been known to be linearly-approximated when it is represented in a double logarithmic plot. Here, as illustrated in FIG. 15, the endotoxin concentration (horizontal axis) and the reaction-starting time (detection time (vertical axis) were plotted in logarithm, respectively. Each plot was represented as an average value of two measurements.

In the usual difference method of the comparative example where the time interval is not changed, endotoxin was detectable when the concentration of endotoxin was in the range of 1.0 to 0.001 EU/mL. However, when the concentration of endotoxin was 0.0001 EU/mL, which is below the above range, the detection was failed because any absorbance difference value was not so high as to exceed the threshold. On the other hand, in the time-function difference method and the multi-series difference method of the present invention, endotoxin could be detected at an extremely wide concentration range of 1.0 to 0.0001 EU/mL. The linearity of plots obtained by the respective techniques for difference (approximate expression and correlation) is listed in Table 1.

TABLE 1

| Method | Approximate expression | Correlation function ($|r|$) |
|---|---|---|
| Usual difference method | $Y = 5.2768X^{-0.3712}$ | 0.9899 |
| Time-function difference method | $Y = 6.5175X^{-0.3085}$ | 0.9989 |
| Multi-series difference method | $Y = 6.9777X^{-0.2881}$ | 0.9993 |

As is evident from FIG. 15 and Table 1, the measurable range of the usual difference method is limited to an endotoxin concentration of 0.001 EU/mL sample. In addition, the correlation coefficient of the usual difference method is lower than those of the other methods. This is supported by a fact that the plot is largely deviated upward from the approximate expression particularly at a concentration of 0.001 EU/mL. On the other hand, in the two difference methods in this embodiment, the deviation of plot from the approximate expression was small and the correlation coefficient was also very good. In particular, in the multi-series difference method, the linearity is extremely good.

Example 7

Exemplary Measurement of Limulus Reagent for Colorimetric Method

Figure 16:
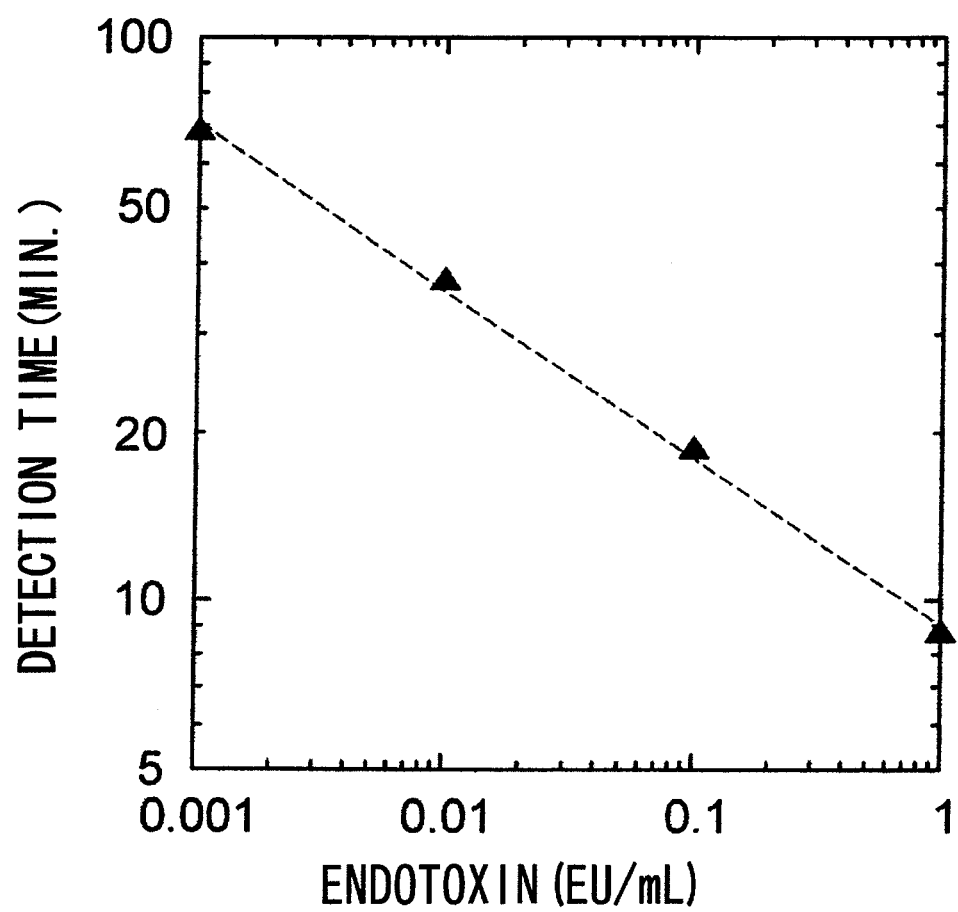
FIG. 16 is a graph illustrating the linearity of calibration curves of endotoxin measurement by a colorimetric method, in a multi-series difference method in accordance with Example 7 of the present invention.

In the present example, a measurement of an endotoxin dilution series (1.0 to 0.001 EU/mL) was performed using Pyrochrome available from Seikagaku Biobusiness Corporation as a Limulus reagent for colorimetric method and using the turbidimetric measurement apparatus 1 (EX-100) used in the above example. The multi-series difference method was used for the detection of endotoxin. The conditions used were exactly the same as those of Example 5. The conditions include: the number of series; a data-sampling interval in each series, the number of elements in a sequence retained in each series; a method for calculating a difference value of absorbance; and so on. A reaction-starting time (detection time) was obtained from the average value of two data and its relationship with the concentration of endotoxin was plotted in double logarithm. As a result, as illustrated in FIG. 16, an extremely high linearity was obtained. The approximate expression was represented by equation (3). A correlation coefficient ($|r|$) of 0.9988 was obtained.

$$Y = 9.0266 X^{-0.2984} \tag{3}$$

Example 8

Example of β-D-Glucan Measurement with β-D-Glucan Measuring Reagent

Figure 17:
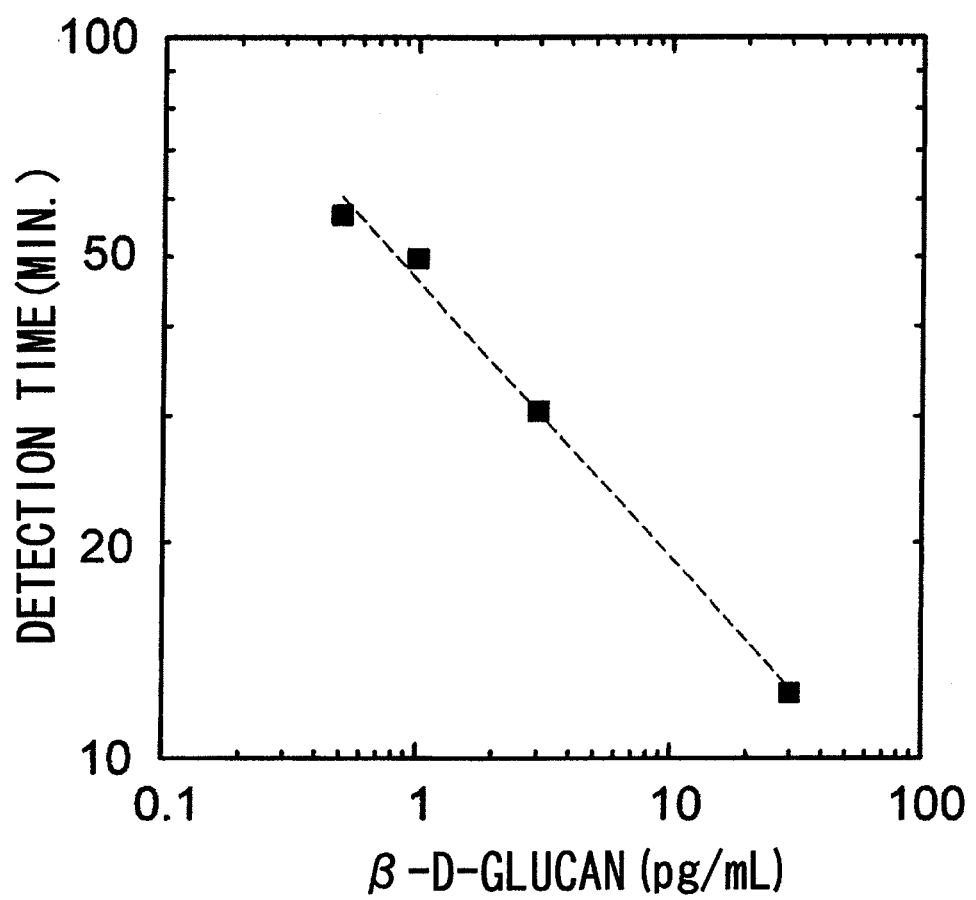
FIG. 17 is a graph illustrating the linearity of calibration curves of β-D-glucan measurement by a stirring turbidimetric method, in a multi-series difference method in accordance with Example 7 of the present invention.

In this example, a β-D-glucan dilution series at a concentration of 30 to 0.5 pg/mL was measured using an external diagnostic agent, β-D-Glucan Test Wako Limulus reagent (manufactured by Wako Pure Chemical Industries, Ltd.). The multi-series difference method used in Example 5 was used for the detection of β-D-glucan. Three series were used. The sampling interval was every 1 second for S1, every 6 seconds for S2, and every 15 seconds for S3. As a result, the difference interval for acquiring the difference was 1 minute for S1, 6 minutes for S2, and 15 minutes for S3. Other measurement conditions were similar to those described in Example 5. The relationship of concentration of β-D-glucan and reaction-starting time (detection time) obtained by the measurement were plotted in double logarithm. As a result, as illustrated in FIG. 17, an extremely high linearity was obtained. The approximate expression was represented by equation (4), where the correlation coefficient ($|r|$) was 0.9970.

$$Y = 46.348 X^{-0.3852} \tag{4}$$

Example 9

Example of Endotoxin Measurement by LAL-Binding Bead Method

In this example, an endotoxin dilution series of 1.0 to 0.001 EU/mL in concentration was measured using a LAL-binding bead method (see, for example, Patent Document 4 cited above). In the LAL-binding bead method, a reagent is prepared such that protein in LAL is absorbed or bonded on beads (fine particles) dispersed in a drug solution previously prepared. Then, a sample containing endotoxin is treated with the reagent to accelerate the formation of a large aggregated cluster at an early stage by coagulation of fine particles. Subsequently, the generation of the aggregated cluster is detected, and the measurement of endotoxin is performed.

Figure 18:
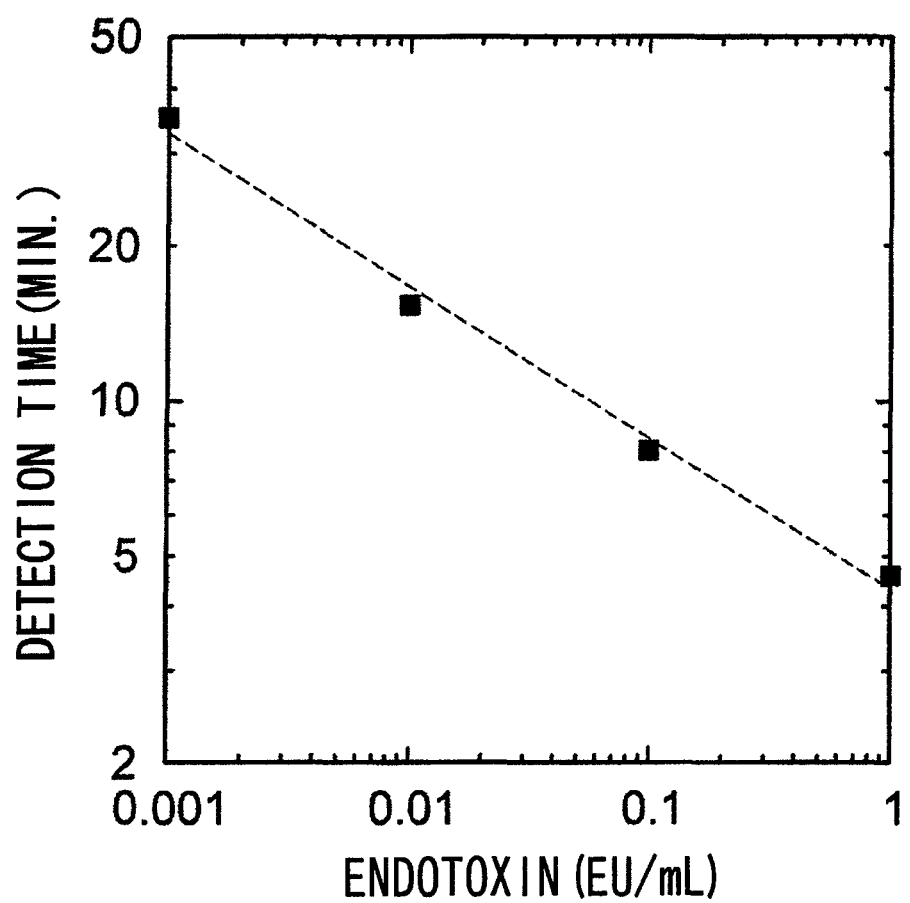
FIG. 18 is a graph illustrating the linearity of the calibration curves of endotoxin measurement when a multi-series difference method is applied to endotoxin measurement by a LAL bead method in accordance with Example 9 of the present invention.

The detection of endotoxin was performed using the multi-series difference method used in Example 5. Three series were used. The same analyzing conditions, such as sampling intervals in the series of S1 to S3, as those of Example 5 were used. On the other hand, in the measurement using LAL-binding beads, a sample, which has been originally turbid, becomes clear while being aggregated because the sample contains a large number of beads as light scattering bodies. In this process, it is preferable to use the difference value of optical transmittance in an aggregation determination rather than the use of the difference value of absorbance. In the present example, therefore, the aggregation determination was performed using the difference value of the optical transmittance, which was different from Example 5. The threshold for the determination was set to 2.0 in all the series of S1 to S3. A relationship between the concentration of endotoxin and a reaction-starting time (detection time) obtained by the measurement was plotted in double logarithm. As a result, as illustrated in FIG. 18, an extremely high linearity was obtained. The approximate expression was represented by equation (5). A correlation coefficient ($|r|$) of 0.9960 was obtained.

$$Y = 4.307 X^{-0.294} \tag{5}$$

Example 10

Example of Endotoxin Measurement Using LAL Reagent for Turbidimetric Method

In this example, an endotoxin measurement using a LAL reagent for turbidimetric method was employed. The detection of endotoxin was performed using the multi-series difference method used in Example 5. Three series were used. The same analyzing conditions, such as sampling intervals in series of S1 to S3, as those of Example 5 were used. Furthermore, when a change in absorbance includes progressive decrease/increase, instead of subtracting an initial difference value in each series as a background value from the difference value at each time, a value to be subtracted was dynamically updated.

Figure 19:
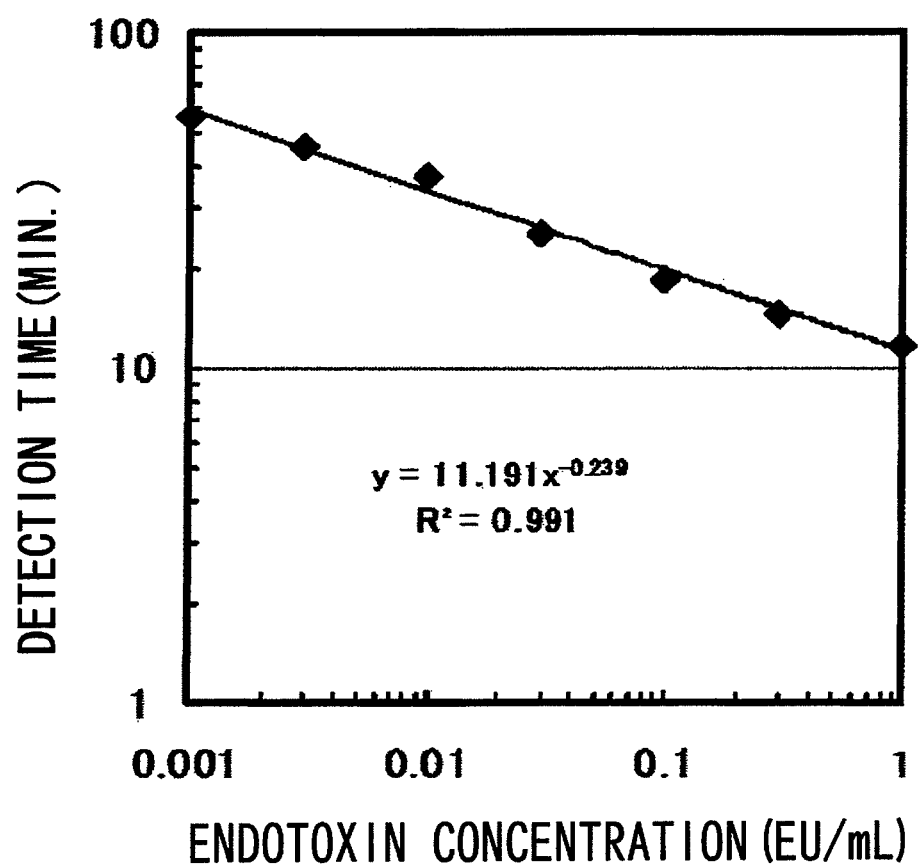
FIG. 19 is a graph illustrating the linearity of calibration curves of endotoxin measurement in the case where a value that serves as a background value to be subtracted from a difference value at each time is dynamically updated when a progressive decrease/increase is observed in a multi-series difference method in accordance with Example 10 of the present invention.

FIG. 19 is an exemplary endotoxin measurement using a LAL reagent for turbidimetric method, "Pyrotell (registered trademark; manufactured by CapeCod, Co., Ltd., and available from Seikagaku Biobusiness Corporation). In this example, in the range of 1 to 0.001 EU/mL, the sampling intervals of the above three series were used to measure an endotoxin dilution series at seven different concentrations.

In the present example, an absorbance difference value was measured every sampling time. The obtained absorbance difference values were rearranged in descending order for every series together with the past sampling times. Lowest five data were updated and recorded. Then, in each series, the third lowest value was used as a reference difference value for each series and subtracted from the absorbance difference value obtained at the time. Subsequently, a detection determination for a reaction-starting time was performed depending on whether the subtracted value exceeded a threshold or not. The threshed was set to 0.01 when the sampling interval was 1 second or 6 seconds (in series S1 and S2) and 0.005 when the sampling interval was 30 seconds (in series S3).

A relationship between the concentration of endotoxin and a reaction-starting time (detection time) obtained by the measurement was plotted in double logarithm. As a result, as illustrated in FIG. 19, an extremely high linearity was obtained. Pyrotell tends to cause a change in difference value sharply. Thus, the method of the present example, which performs determination while changing a value to be subtracted from a difference value at each time as needed, may be effective when a change in absorbance includes progressive decrease/increase. The approximate expression was represented by equation (6), where the correlation coefficient (|r|) was 0.9955.

$$Y = 11.191 X^{-0.239} \tag{6}$$

Figure 20:
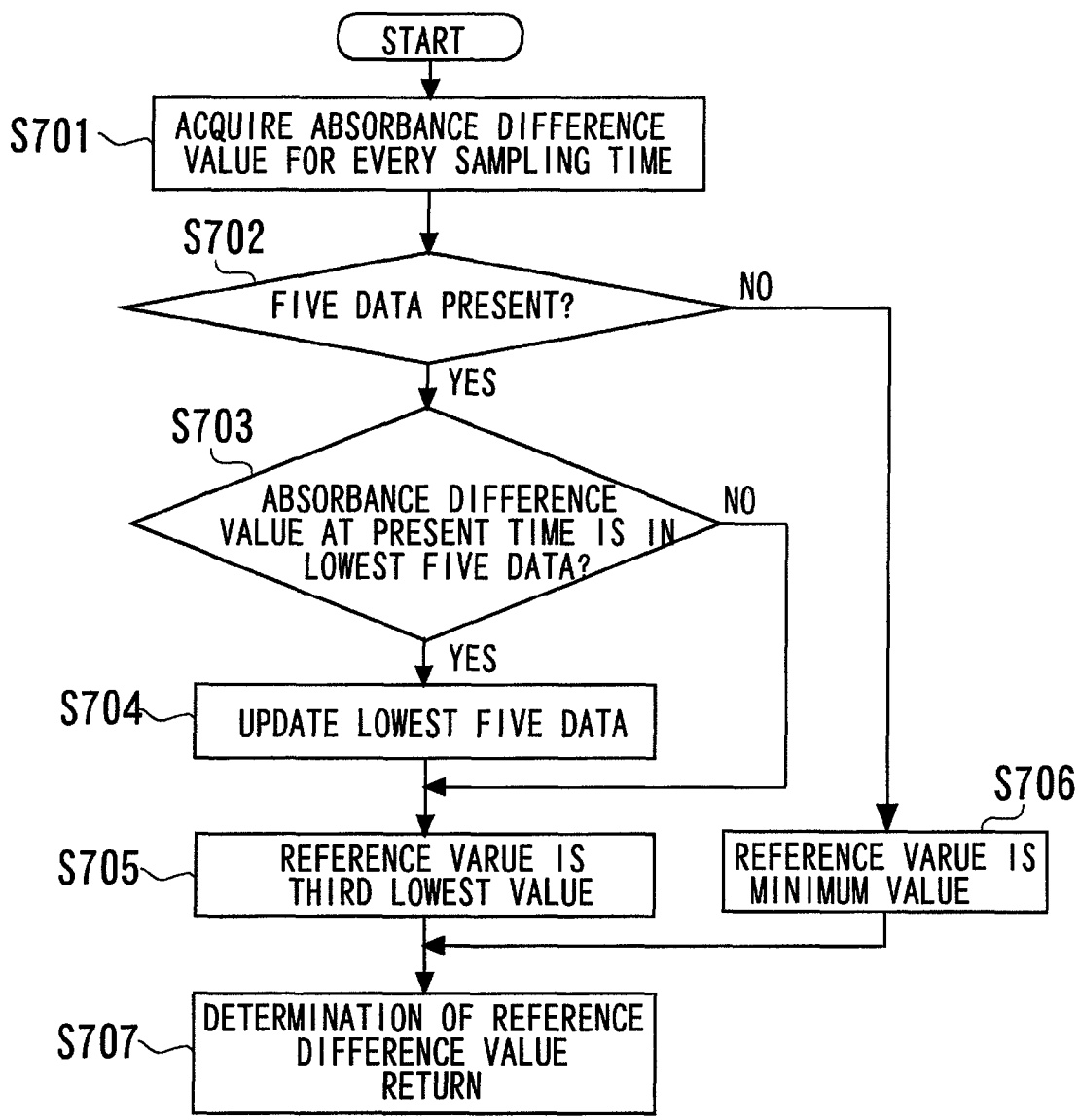
FIG. 20 is a flowchart illustrating a subroutine for calculating a reference difference value in accordance with Example 10 of the present invention.
Figure 21:
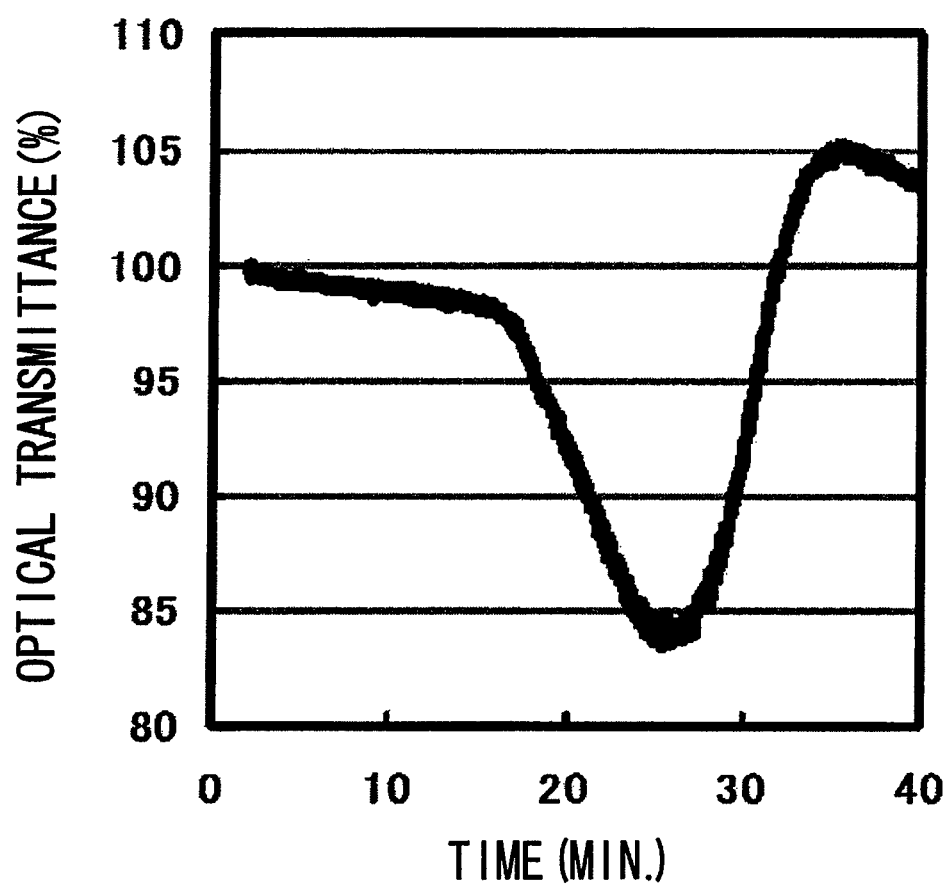
FIG. 21 is a graph illustrating an exemplary change in optical transmittance over time by an endotoxin reaction when a progressive decrease/increase is observed.

FIG. 20 illustrates a subroutine for calculating a reference difference value in the present example. In the present example, this subroutine for calculating a reference difference value is a subroutine to be executed in processing in S214, S224, and S234 when the measurement routine 2 illustrated in FIG. 14 is executed. First, when the present routine is executed, an absorbance difference value is acquired every sampling time in S701.

In S702, it is determined whether five data of the absorbance difference value are present or not. Here, when an affirmative decision is made, the process proceeds to S703. On the other hand, when a negative decision is made, the process proceeds to S706. In S703, it is determined whether the absorbance difference value at the present time is included in the lowest five values or not. Here, when an affirmative decision is made, the process proceeds to S704. On the other hand, when a negative decision is made, the process proceeds to S705.

In S704, newly acquired data is added to the lowest five data and the lowest five data are then updated. When the processing in S704 is completed, the process proceeds to S705. In S705, the third lowest data at the present time is set as a reference difference value. Here, in S706, the minimum data at the time is set as a reference difference value. After the processing of S705 or S706 is completed, the process proceeds to S707. In S707, a reference difference value is determined and stored. Then the process returns to the main routine of the measurement routine 2. Here, the flowchart of the subroutine for calculating a reference difference value illustrated in FIG. 20 is an exemplary routine for performing the measurement of the present example. Thus, it is contemplated that the measurement routine is not limited to the flow represented in any of these flowcharts.

The above examples have been described as those in which the present invention is applied to the stirring turbidimetric method using the turbidimetric measurement apparatus 1. It goes without saying that the present invention is applicable to a turbidimetric method without depending on stirring, a measurement method other than a stirring turbidimetric method and a measurement vessel. The above examples have been described as those in which a reaction-starting time is defined as a time at which physical quantity, such as absorbance, exceeds a threshold. However, the reaction-starting time may be a time at which physical quantity, such as absorbance, is equal to or more than a threshold. Alternatively, the reaction-starting time may be a time at which physical quantity, such as transmitted light intensity, scattered light intensity, the number of light scattering particles, fluorescence intensity, or chemiluminescence intensity, exceeds a threshold or at a time it becomes equal to or more than the threshold.

Furthermore, in the above examples, when the absorbance is employed as a detected value, a reaction-starting time is defined as a time at which an absorbance difference between two acquisition times exceeds a threshold. However, in the case of employing an optical transmittance as a detected value, for example, a detected value becomes small with time. In this case, therefore, the reaction-starting time may be a time at which the absolute value of the difference of optical transmittance between the two acquisition times exceeds a threshold.

Furthermore, in the above examples, as a detected value or a difference value at one acquisition time, the average value or the median value of data including a plurality of data before and after the acquisition time may be employed in fact. Furthermore, data may be rearranged in descending order and the numerical values with specified rankings may be used. In this case, the noise influence on the detected value or difference value at each acquisition time can be reduced. Thus, the measurement can be performed with higher accuracy. For example, 30 to 40 data in total before and after the acquisition time may be averaged and the detected value or difference value may be obtained as the averaged value at this acquisition time.

Furthermore, in the above example, when determining whether the difference value exceeds the threshold or not, it is preferably determined that the difference value exceeds the threshold when the difference values at a plurality of acquisition times continuously exceed the threshold. Therefore, it becomes possible to reduce an influence of noise on the determination of a reaction-starting time and improve the accuracy of endotoxin measurement more reliably.

| DESCRIPTION OF REFERENCE NUMERALS | |
|---|---|
| 1 | turbidimetric measurement apparatus |
| 2 | glass vessel |
| 3 | stirring bar |
| 4 | stirrer |
| 4a | motor |
| 4b | magnet |
| 5 | warmer |
| 5a | light incident hole |
| 5b | emission hole |
| 6 | light source |
| 7 | aperture |
| 8 | aperture |
| 9 | light receiving element |
| 10 | arithmetic unit |
| 11 | measurement system |
| 12 | light source |
| 13 | incidence optical system |
| 14 | sample cell |
| 15 | output optical system |
| 16 | light receiving element |
| 17 | amplifying circuit |
| 18 | denoising filter |
| 19 | arithmetic unit |
| 20 | display unit |
| 21 | stirring bar |
| 22 | stirrer |

What is claimed is:

1. A method for measuring a physiologically active substance of biological origin, comprising:
   mixing a limulus amoebocyte lysate, LAL, with a sample containing a predetermined physiologically active substance of biological origin;
   acquiring, after the mixing, a predetermined physical quantity, which varies due to the reaction between LAL and the physiologically active substance, continuously as a detected value;
   defining one acquisition time as a reaction-starting time when a difference between a detected value at the one acquisition time and a detected value at a previous acquisition time before a predetermined time interval from the one acquisition time or an absolute value of the difference becomes not less than or exceeds a previously defined threshold; and
   detecting the physiologically active substance in the sample or measuring the concentration of the physiologically active substance, based on the reaction-starting time.

2. The method for measuring a physiologically active substance of biological origin according to claim 1, wherein
   the physiologically active substance of biological origin in the sample is reacted with a limulus amoebocyte lysate, LAL to detect the physiologically active substance in the sample or measure the concentration of the physiologically active substance,
   after mixing the sample and LAL, light is incident on a liquid mixture of the sample and LAL,
   among the incident light, the intensity of light having passed through the liquid mixture or light scattered on the liquid mixture is acquired,
   a predetermined physical quantity which is acquired by the intensity of the acquired light at an acquisition time set up with a predetermined time interval, is defined as a detected value, and
   a reaction-starting time is defined as a time at which a difference between the detected value at the one acquisition time and a detected value at a previous acquisition time or the absolute value of the difference exceeds the threshold.

3. The method for measuring a physiologically active substance of biological origin according to claim 2, wherein
   the acquired light intensity is the intensity of light having passed through the liquid mixture,
   the detected value is a transmittance of the liquid mixture expressed in percentage,
   the predetermined time interval is set to about 2 minutes, and
   the reaction-starting time is defined as a time at which an absolute value of a difference between the transmittance at the one acquisition time and the transmittance obtained at the previous acquisition time exceeds 1.

4. The method for measuring a physiologically active substance of biological origin according to claim 2, wherein
   the intensity of the acquired light is the intensity of light scattered by the liquid mixture,
   the detected value is the number of particles that scatter the light incident on the liquid mixture and is derived based on a predetermined number of peaks of the intensity of the scattered light,
   the predetermined time interval is set to about 100 seconds, and
   the reaction-starting time is defined as a time at which a difference between the number of particles at the one acquisition time and the number of particles at the previous acquisition time exceeds 200.

5. The method for measuring a physiologically active substance of biological origin according to claim 1, wherein
   the predetermined time interval is changed with reference to the one acquisition time.

6. The method for measuring a physiologically active substance of biological origin according to claim 5, wherein
   light is incident on a liquid mixture comprising the LAL and the sample,
   among the incident light, the intensity of light having passed through the liquid mixture or one scattered on the liquid mixture is continuously detected, and
   any one of optical transmittance, absorbance, scattered light intensity, number of light scattering particles, fluorescence intensity, and chemiluminescence intensity, which is acquired from the intensity of the light continuously detected, is used as a detected value.

7. The method for measuring a physiologically active substance of biological origin according to claim 6, wherein
   the later the one acquisition time becomes, the longer the predetermined time interval is set.

8. The method for measuring a physiologically active substance of biological origin according to claim 6, wherein
   there is provided a plurality of series of acquisition times of the predetermined physical quantity each having the predetermined time interval set constant, where the predetermined time intervals of the respective series are different from one another, and
   the series to be used is changed with reference to the one acquisition time.

9. A computer program product comprising a non-transitory storage medium having stored thereon executable program code that directs a computer system to perform the method of claim 6.

10. The method for measuring a physiologically active substance of biological origin according to claim 5, wherein
    the later the one acquisition time becomes, the longer the predetermined time interval is set.

11. A computer program product comprising a non-transitory storage medium having stored thereon executable program code that directs a computer system to perform the method of claim 10.

12. The method for measuring a physiologically active substance of biological origin according to claim 5, wherein
there is provided a plurality of series of acquisition times of the predetermined physical quantity each having the predetermined time interval set constant, where the predetermined time intervals of the respective series are different from one another, and
the series to be used is changed with reference to the one acquisition time.

13. The method for measuring a physiologically active substance of biological origin according to claim 12, wherein
the series to be used is one in which a difference between a detected value at the one acquisition time and a detected value at a previous acquisition time before a predetermined time interval from the one acquisition time or the absolute value of the difference is the highest.

14. A computer program product comprising a non-transitory storage medium having stored thereon executable program code that directs a computer system to perform the method of claim 13.

15. The method for measuring a physiologically active substance of biological origin according to claim 12, wherein
a plurality of differences or the absolute values thereof, in which each difference is of between a detected value at the one acquisition time and a detected value at a previous acquisition time before a predetermined time interval from the one acquisition time, is acquired at different acquisition times,
the resulting differences are lined up in descending order and a value at a rank other than the last is defined as a reference difference value,
the reference difference value is subtracted from the difference or the absolute value thereof, and
when the resulting value is equal to or higher than the threshold or exceeds the threshold, the one acquisition time is defined as the reaction-starting time.

16. A computer program product comprising a non-transitory storage medium having stored thereon executable program code that directs a computer system to perform the method of claim 15.

17. A computer program product comprising a non-transitory storage medium having stored thereon executable program code that directs a computer system to perform the method of claim 12.

18. A computer program product comprising a non-transitory storage medium having stored thereon executable program code that directs a computer system to perform the method of claim 5.

19. The method for measuring a physiologically active substance of biological origin according to claim 1, wherein
the physiologically active substance of biological origin is endotoxin or β-D-glucan.

20. An apparatus for measuring a physiologically active substance of biological origin, comprising:
a liquid mixture retaining device for retaining liquid mixture of a sample containing a predetermined physiologically active substance of biological origin and a limulus amoebocyte lysate, LAL, while allowing light to be incident on the liquid mixture and for promoting a reaction in the liquid mixture;
a stirring device for stirring the liquid mixture in the liquid mixture retaining device;
a light incidence device for entering light into the liquid mixture in the liquid mixture retaining device;
a light receiving device for receiving transmitted light or scattered light of the incident light from the liquid mixture and converting the transmitted light or the scattered light into an electric signal;
a determining device for determining a reaction-starting time between the physiologically active substance and LAL in the sample from the electric signal converted in the light receiving device; and
a deriving device s for deriving an existence or concentration of the physiologically active substance in the sample with reference to a relationship set in advance between the reaction-starting time and the concentration of the physiologically active substance, wherein
the determining device determines a reaction-starting time as a time at which a difference between a detected signal value at one acquisition time among acquisition times set at predetermined time intervals, where a signal obtained by subjecting the electric signal to a predetermined calculation or the electric signal itself is used as a detected signal value, and a detected signal value at a previous acquisition time or an absolute value of the difference becomes not less than or exceeds a previously defined threshold.

21. The apparatus for measuring a physiologically active substance of biological origin according to claim 20, wherein
the detected signal value is a transmittance of the liquid mixture expressed in percentage,
the predetermined time interval is about 2 minutes, and
the threshold is 1.

22. The apparatus for measuring a physiologically active substance of biological origin according to claim 20, wherein
the detected signal value is the number of particles that scatter the light incident on the liquid mixture, and
the predetermined time interval is about 100 seconds, and
the threshold is 200.

23. The apparatus for measuring a physiologically active substance of biological origin according to claim 20, wherein
the predetermined time interval and/or the threshold is variable.

24. The apparatus for measuring a physiologically active substance of biological origin according to claim 20, wherein
the determining device changes the predetermined time interval with reference to the one acquisition time.

25. The apparatus for measuring a physiologically active substance of biological origin according to claim 24, wherein
the determining device sets the predetermined time interval so that the later the one acquisition time becomes, the longer the predetermined time interval becomes.

26. The apparatus for measuring a physiologically active substance of biological origin according to claim 25, wherein
the determining device includes a plurality of series of acquisition times of the transmitted or scattered light each having the predetermined time interval set constant, where the predetermined time intervals of the respective series are different from one another, and
the series to be used is changed with reference to the one acquisition time.

27. The apparatus for measuring a physiologically active substance of biological origin according to claim 26, wherein
the series to be used is one in which a difference between a detected value at the one acquisition time and a detected value at a previous acquisition time before a predetermined time interval from the one acquisition time or the absolute value of the difference is the highest.

28. The apparatus for measuring a physiologically active substance of biological origin according to claim 26, wherein
- a plurality of differences or the absolute values thereof, in which each difference is of between a detected value at the one acquisition time and a detected value at a previous acquisition time before a predetermined time interval from the one acquisition time, is acquired at different acquisition times,
- the resulting differences are lined up in descending order and a value at a rank other than the last is defined as a reference difference value,
- the reference difference value is subtracted from the difference or the absolute value thereof, and
- a time at which the resulting value of the subtraction becomes not less than or exceeds the threshold is defined as a reaction-starting time.

29. The apparatus for measuring a physiologically active substance of biological origin according to claim 20, wherein
- the physiologically active substance of biological origin is endotoxin or β-D-glucan.

* * * * *

UNITED STATES PATENT AND TRADEMARK OFFICE
CERTIFICATE OF CORRECTION

| | | |
|---|---|---|
| PATENT NO. | : 8,507,282 B2 | Page 1 of 1 |
| APPLICATION NO. | : 13/256427 | |
| DATED | : August 13, 2013 | |
| INVENTOR(S) | : Yabusaki et al. | |

It is certified that error appears in the above-identified patent and that said Letters Patent is hereby corrected as shown below:

In the Specification

In column 12 at line 19, Change "alight" to --a light--.

In column 13 at line 20, Change "endototin" to --endotoxin--.

In the Claims

In column 38 at line 11, In Claim 20, Change "device s" to --devices--.

Signed and Sealed this
Thirteenth Day of May, 2014

Michelle K. Lee
*Deputy Director of the United States Patent and Trademark Office*